(12) United States Patent
Sato

(10) Patent No.: US 6,743,630 B2
(45) Date of Patent: Jun. 1, 2004

(54) METHOD OF PREPARING A PROTEIN ARRAY BASED ON BIOCHEMICAL PROTEIN-PROTEIN INTERACTION

(75) Inventor: Taka-Aki Sato, Fort Lee, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 10/092,138

(22) Filed: Mar. 6, 2002

(65) Prior Publication Data

US 2003/0170723 A1 Sep. 11, 2003

(51) Int. Cl.$^7$ .................................................. C12N 5/00

(52) U.S. Cl. ...................... 435/402; 435/397; 435/396; 435/395; 435/DIG. 49; 435/DIG. 46

(58) Field of Search ................................. 435/402, 397, 435/396, 395, DIG. 49, DIG. 46, 7.1; 310/350

(56) References Cited

U.S. PATENT DOCUMENTS

| | | | |
|---|---|---|---|
| 5,632,994 A | 5/1997 | Reed et al. | 424/198.1 |
| 5,747,245 A | 5/1998 | Reed et al. | 435/6 |
| 5,783,666 A | 7/1998 | Abertsen et al. | 530/350 |
| 5,876,939 A | 3/1999 | Reed et al. | 435/6 |
| 2002/0058607 A1 | 5/2002 | Sato et al. | |

FOREIGN PATENT DOCUMENTS

| | | |
|---|---|---|
| JP | 9-512598 | 9/1999 |
| WO | 95/34661 | 12/1995 |
| WO | 96/18641 | 6/1996 |
| WO | 97/11091 | 3/1997 |

OTHER PUBLICATIONS

Comparative and Functional Genomics (2001), 2(55), 307–309, Schneider.*
Jrn. of Cell Science, (2001), 114(18), 3219–31, Harris et al.*
Desjardins, P., et al. (1990) "Sequence and Gene Organization of the Chicken Mitochondrial Genome", *J. Mol. Biol.*, 212:599–634.
Itoh, N., et al. (1991) "The Polypeptide Encoded by the cDNA for Human Cell Surface Antigen Fas Can Mediate Apoptosis", *Cell*, 66:233–243.
Watanabe–Fukunaga, R., et al. (1991) "Lymphoproliferation disorder in mice explained by defects in Fas antigen that mediates apoptosis", *J. Cell Biol.*, 115:1039–1048.
Woods, D. F., et al. (1991) "The Discs–Large Tumor Suppressor Gene of Drosophila Encodes a Guanylate Kinase Homolog Localized at Separate Junctions", *Cell*, 66:451–464.
Cho, K–O., et al. (1992) "The Rat Brain Postsynaptic Density Fraction Contains a Homolog of the Drosophila Discs–Large Tumor Suppressor Protein", *Neuron*, 9:929–942.

Okimoto, R., et al. (1993) "The Mitochondrial Genomes of Two Nematodes, *Caenorhabditis elegans* and *Ascaris suum*", *Genetics*, 130:471–498.
Itoh, N., et al. (1993) "A Novel Protein Domain Required for Apoptosis", *J. Mol. Biol.*, 268:10932–10937.
Banville, D., et al. (1994) "A Novel Protein–Tyrosine Phosphatase with Homology to Both the Cytoskeletal Proteins of the Band 4.1 Family and Junction–associated Guanylate Kinases", *J. Biol. Chem.*, 269:22320–22327.
Kitamura, K., et al. (1994) "Identification and hypotensive activity of proadrenomedullin N–terminal 20 peptide (PAMP)", *FEBS Letters*, 351:35–37.
Maekawa, K., et al. (1994) "Molecular cloning of a novel protein–tyrosine phosphatase containing a membrane–binding domain and GLGF repeats", *FEBS Letters*, 337:200–206.
Saras, J., et al. (1994) "Cloning and Characterization of PTPL1, a Protein Tyrosine Phosphatase with Similarities to Cytoskeletal–associated Proteins", *J. Biol. Chem.*, 269:24082–24089.
Takahashi, T., et al. (1994) "Generalized Lymphoproliferative Disease in Mice, Caused by a Point Mutation in the Fas Ligand", *Cell*, 76:969–976.
Boldin, M. P., et al. (1995) "A Novel Protein That Interacts with the Death Domain of Fas/APO1 Contains a Sequence Motif Related to the Death Domain", *J. Biol. Chem.*, 270:7795–7798.
Chao, M. V., et al. (1995) "p75 and Trk: a two–receptor system", *TINS*, 18:321–326.
Chinnaiyan, A. M., et al. (1995) "FADD, a Novel Death Domain–Containing Protein, interacts with the Death Domain of Fas and Initiates Apoptosis", *Cell*, 81:505–512.
Kim, E., et al. (1995) "Clustering of Shaker–type K$^+$ channels by interaction with a family of membrane–associated guanylate kinases", *Nature*, 378:85–88.
Kischkel, F. C., et al. (1995) "Cytotoxicity–dependent APO–1 (Fas/CD95)—associated proteins form a death–inducing signaling complex (DISC) with the receptor", *EMBO Journal*, 14:5579–5588.

(List continued on next page.)

*Primary Examiner*—T. D. Wessendorf
(74) *Attorney, Agent, or Firm*—John P. White; Cooper & Dunham LLP

(57) ABSTRACT

A method of preparing a protein array based on biochemical protein-protein interaction is provided. An array of a first protein which includes a PDZ domain is deposited on a substrate. A second protein, which includes an amino acid sequence (S/T)—X—(V/I/L)—COOH (each hyphen represents a peptide bond, each parenthesis encloses amino acids which are alternatives to one other, each slash within such parentheses separates the alternative amino acids, and the X represents any amino acid which is selected from the group comprising the twenty naturally occurring amino acids), is applied to the first protein array. The amino acid sequence (S/T)—X—(V/I/L)—COOH of the second protein is bound to the PDZ domain of the first protein.

16 Claims, 28 Drawing Sheets

OTHER PUBLICATIONS

Kornau, H–C., et al. (1995) "Domain Interaction Between NMDA Receptor Subunits and the Postsynaptic Density Protein PSD–95", *Science*, 269:1737–1740.

McGahon, A. J., et al. (1995) "The End of the (Cell) Line: Methods for the Study of Apoptosis in Vitro", *Methods in Cell Biology*, 46:153–185.

Pantel, K., et al. (1995) "Establishment of Micrometastatic Carcinoma Cell Lines: a Novel Source of Tumor Cell Vaccines", *J. Natl. Cancer Inst.*, 87:1162–1168.

Sato, T., et al. (1995) "FAP–1: A Protein Tyrosine Phosphatase That Associates with Fas", *Science*, 268:411–415.

Stanger, B. Z., et al. (1995) "RIP: A Novel Protein Containing a Death Domain That Interacts with Fas/APO–1 (CD95) in Yeast and Causes Cell Death", *Cell*, 81:513–523.

Wang, X. W., et al. (1995) "Abrogation of p53–induced Apoptosis by the Hepaatitis B Virus X Gene[1]", *Cancer Res.*, 55:6012–6016.

Westendorp, M. O., et al. (1995) "Sensitization of T cells to CD95–mediated apoptosis by HIV–1 Tat and gp120", *Nature*, 375:497–500.

Doyle, D. A., et al. (1996) "Crystal Structures of a Complexed and Peptide–Free Membrane Protein–Binding Domain: Molecular Basis of Peptide Recognition by PDZ", *Cell*, 85:1067–1076.

Matsumine, A., et al. (1996) "Binding of APC to the Human Homolog of the Drosophila Discs Large Tumor Suppressor Protein", *Science*, 272:1020–1023.

Parker, W., et al. (1996) "The Surface of β–Sheet Proteins Contains Amphiphilic Regions Which May Provide Clues About Protein Folding", Proteins, 25:253–260.

Zhang, J., et al. (1996) "A Mouse Fas–Associated Protein with Homology to the Human Mort1/FADD Protein Is Essential for Fas–Induced Apoptosis", *Molecular And Cell Biology*, 16:2756–2763.

Silzel, J. W., et al. (1998) "Mass–sensing, Multianalyte microarray immunoassay with imaging detection", *Clinical Chemistry*, 44(9):2036–2043.

Pal, D., et al. (1999) "Estimates of the Loss of Main–Chain Conformational Entropy of Different Residues on Protein Folding", *Proteins*, 36:332–339.

Arenkov, P., et al. (2000) "Protein Microchips: Use for Immunoassay and Enzymatic Reactions", *Analytical Biochemistry*, 278:123–131.

Mendoza, L.G., et al. (1999) "High–throughput microarray–based enzyme–linked immunosorbent assay (ELISA)", *Biotechniques*, 27(4)778–780, 782–786, 788.

Rowe, C.A., et al. (1999) "An array immunosensor for simultaneous detection of clinical analytes", *Analytical Biochemistry*, 71(2):433–439.

* cited by examiner

FIG. 2A
Construction of
pBTM116 (LexA)-(X)15
↓
Library DNAs of
pBTM116 (LexA)-(X)15    →    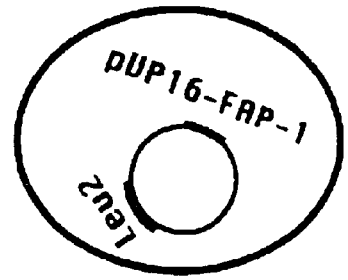
Large scale transformation
of yeast L40
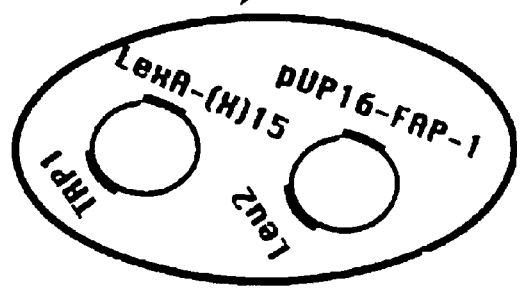
↓
His+, β-gal+
↓
Curing of pVP16-FAP-1
↓
Isolation of
pBTM116 (LexA)-(X)15
↓
Analysis of
DNA sequences

FIG. 2B

Human  D S E N S N F R N E I Q S L V
Rat    S I S N R N E N E G Q S L E
Mouse  S T P D T G N E N E G Q C L E

| | | | | |
|---|---|---|---|---|
| C Y A | | | A I G | L | V | 12-0 |
| E N A | | | G V S | E | V | 5-0 |
| W W G | | | A T Q | P | V | 13-0 |
| E H A | | | Q Q | Q | V | 20-0 |
| N S S | | | F H S | L | V | 6-2 |
| G L R | | | L P P | D | V | 9-5 |
| K S D | | | S G V | N | V | 18-1 |
| G K K | | | R P V | N | V | 22-1 |
| T G K | | | D V W | A | V | 71-1 |
| A S R | | | N E E | L | I | 14-5 |

FIG. 2D

| | |
|---|---|
| I P P D S E D G N E E Q S L V | 8-1 |
| D S E M Y N F R S Q L A S V | 9-3 |
| I D L A S E F L F L S N S F L | 14-1 |
| P P T C S Q A N S G R I S T L | 0-2 |
| S D S N M N E L S E V | 57-5 |
| Q N F R T Y I V S F V | 72-1 |
| R E T I E S T V | 25-9 |
| R G F I S S L V | 16-13 |
| T I Q S V I | 6-3 |
| E S L V | 18-1 |

Consensus: t S-X-V/L/I

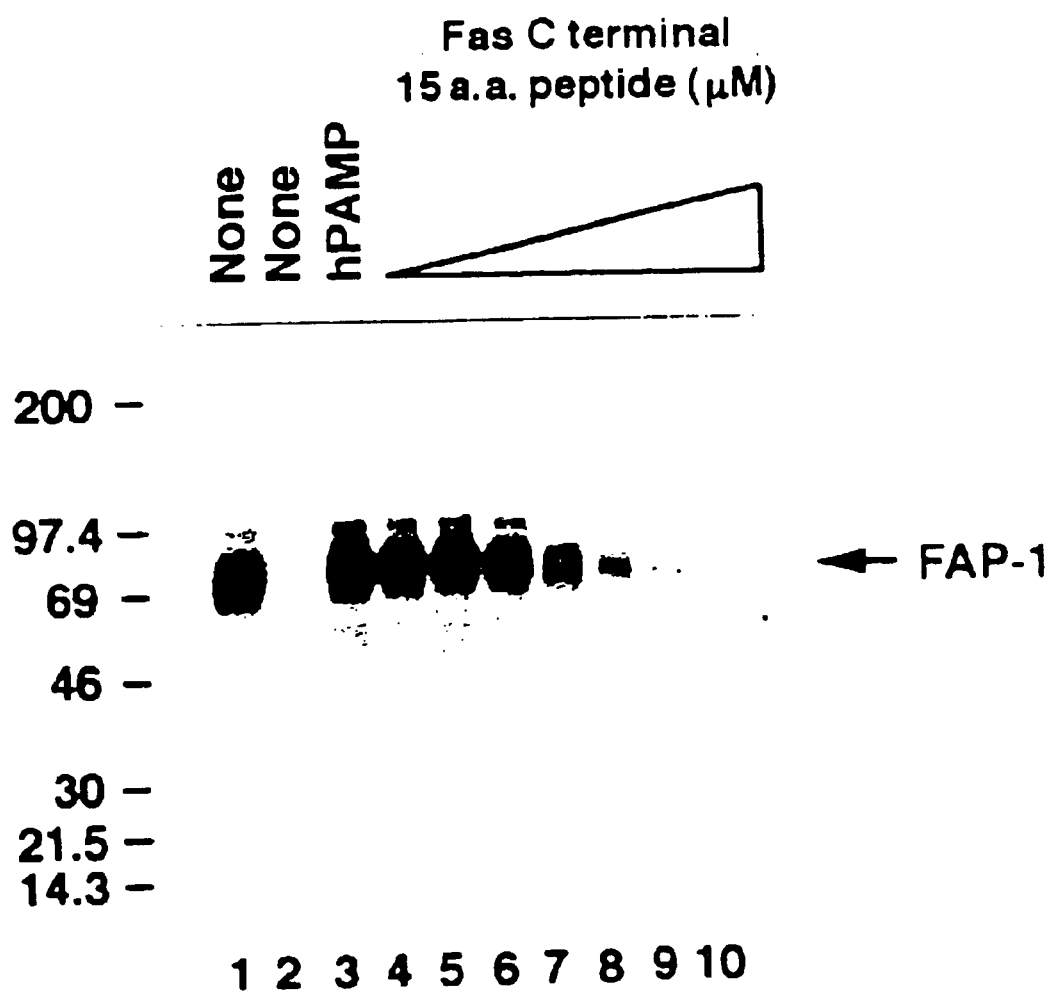

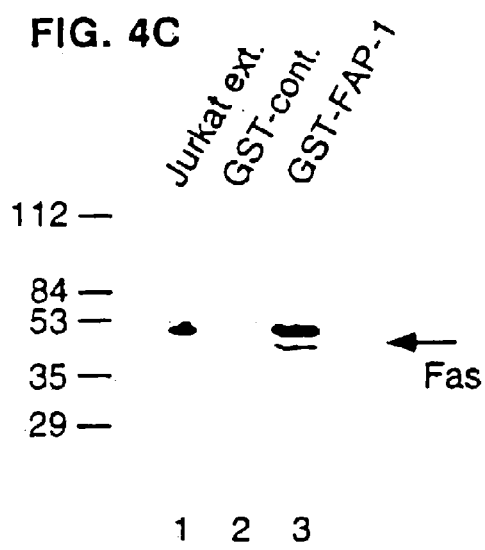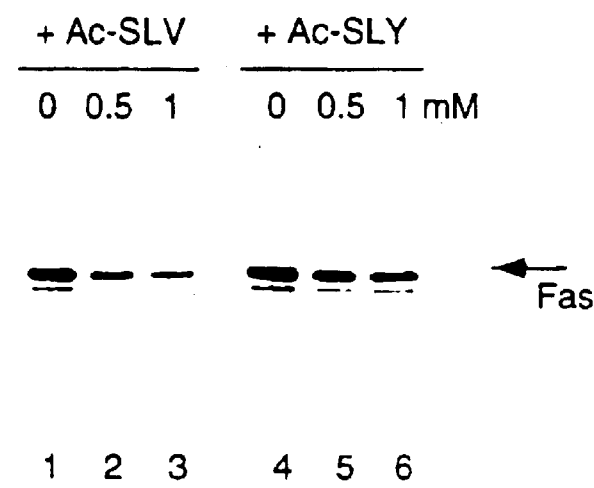

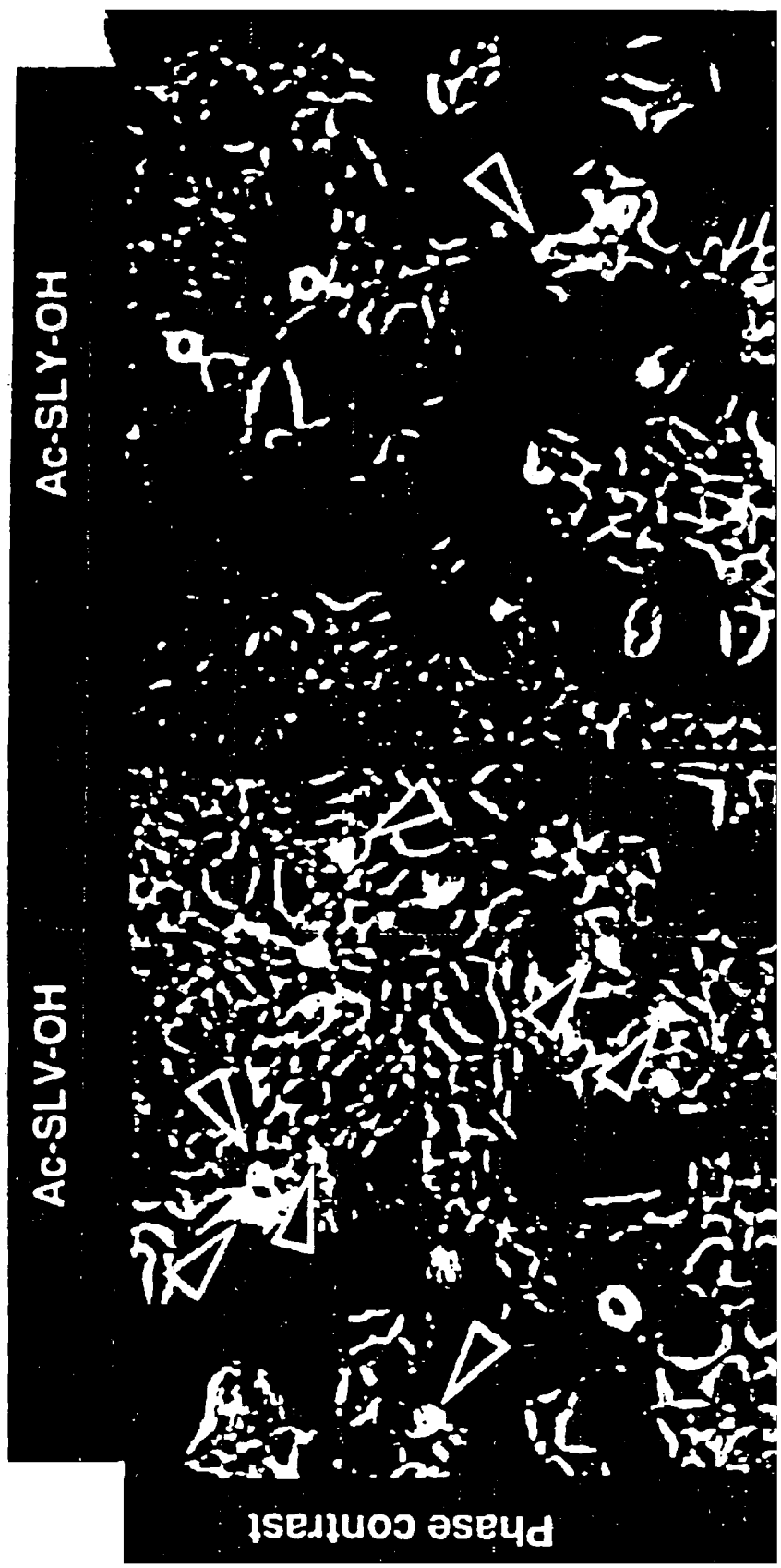

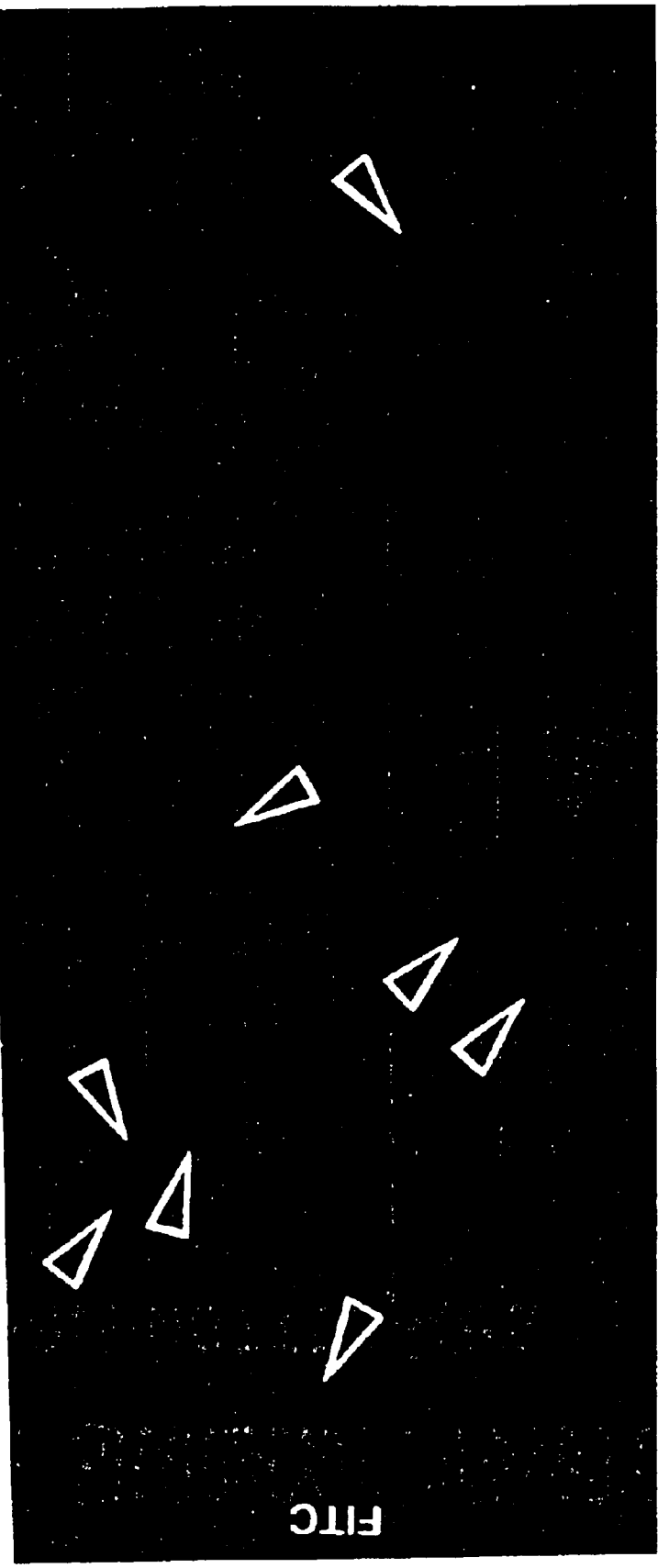

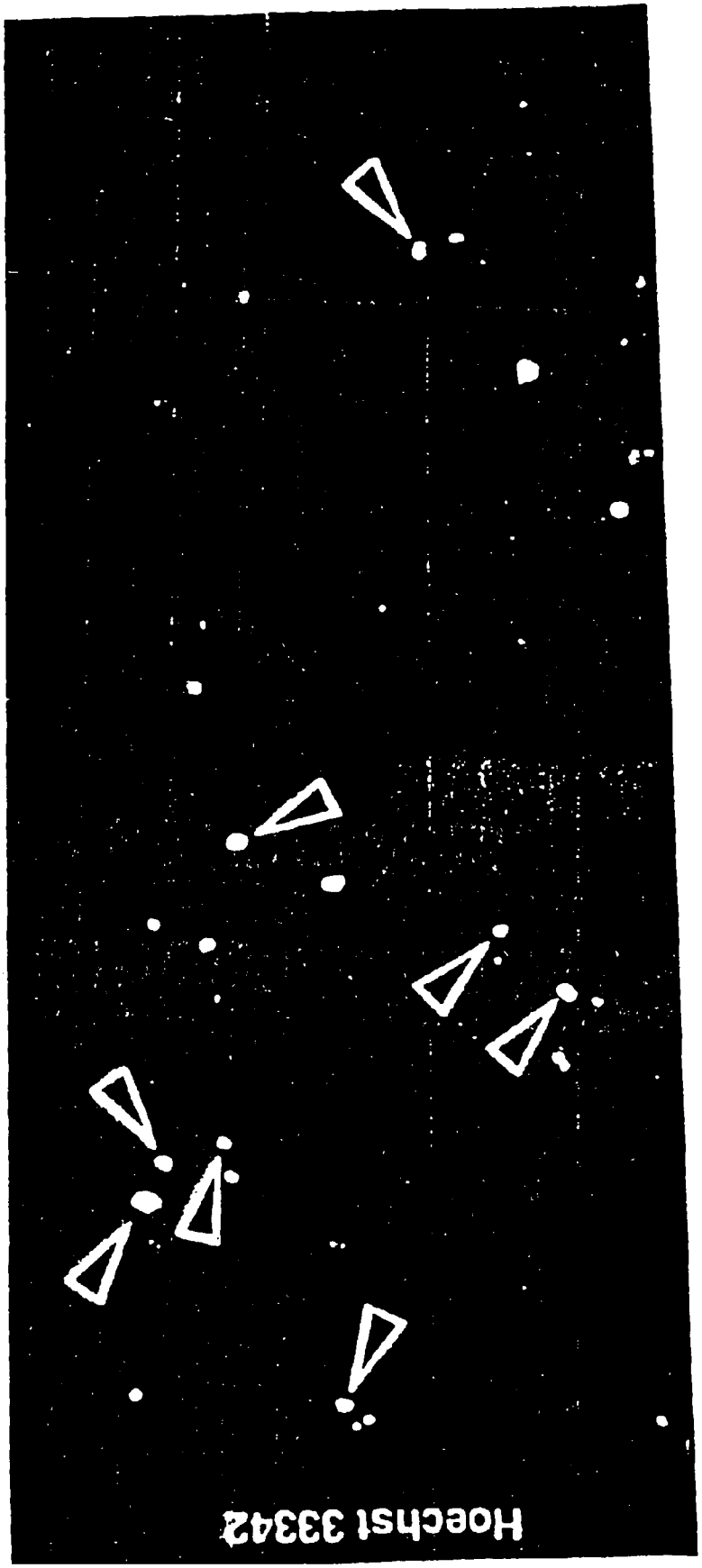

FIG. 7A

NGF Receptor

```
  1 mgagatgram dgprllllll lgvslggake acptglyths gecckacnlg egvaqpcgan
 61 qtvcepclds vtfsdvvsat epckpctecv glqsmsapcv eaddavcrca ygyyqdettg
121 rceacrvcea gsglvfscqd kqntvceecp dgtysdeanh vdpclpctvc edterqlrec
181 trwadaecee ipgrwitrst ppegsdstap stqepeappe qdliastvag vvttvmgssq
241 pvvtrgttdn lipvycsila avvglvayi afkrwnsckq nkqgansrpv nqtpppegek
301 lhsdsgisvd sqslhdqqph tqtasgqalk gdgglysslp pakreevekl lngsagdtwr
361 hlagelgyqp ehidsfthea cpvrallasw atqdsatlda llaalrrigr adlveslcse
421 statspv
```

FIG. 7B

CD4 Receptor

```
  1 mnrgvpfrhl llvlqlallp aatqgkkvvl gkkgdtvelt ctasqkksiq fhwknsnqik
 61 ilgnqgsflt kgpsklndra dsrrslwdgg nfpliiknlk iedsdtyice vedqkeevql
121 lvfgltansd thllqggslt ltlesppgss psvqcrsprg kniqgktls vsqlelqdsg
181 twtctvlqnq kkvefkidiv vlafqkassi vykkegeqve fsfplaftve kltgsgelww
241 qaerassks witfdlknke vsvkrvtqdp klqmgkklpl hltlpqalpq yagsgnltla
301 leaktgklhq evnlvvmrat qlqknltcev wgptspklml slklenkeak vskrekavvv
361 lnpeagmwqc llsdsgqvll esnikvlptw stpvqpmali vlggvaglll figlgiffcv
421 rcrhrrrqae rmsqikrlls ekktcqcphr fqktcspi
```

FIG. 7C

| Species | C-terminal sequences of NGFR (p75) | Binding activity of FAP-1 |
|---------|------------------------------------|---------------------------|
| Human   | SESTATSPV-COOH                     | +                         |
| Rat     | SESTATSPV-COOH                     | +                         |
| Chicken | SESTATSPV-COOH                     | +                         |

FIG. 7D

```
  1 mnsgvamkyg ndssaelsel hsaalaslkg divelnkrlq qtererdlle kklakaqceq
 61 shlmrehedv qertlryee ritelhsvia elnkkidrlq gttireedey selrselsqs
121 qhevnedsrs mdqdqtsvsi pengstmvta dmdncsdins elqrvitgle nvvcgrkkss
181 cslsvaevdr hieqlttase hcdlaiktve elegvlgrdl ypnlaeersr wekelagire
241 enesltamlc skeeeinrtk atmnaireer drlrrrvrel qtrlqsvqat gpsspgrits
301 tnrplnpstg elststssnd lplaklaerv klsktrsess ssdrpvlgse lssigvsssv
361 aehiahslqd csnlqeifqt lyshgsalge skirefevet erlnsriehl ksqmdlltit
421 leecksnaer msmlvgkyes natalrlalq yseqcieaye lllalaeseq slilgcfraa
481 gvgsspgdqs gdenltqmlk rahdcrktae naakalimkl dgscggafav agcsvqpwes
541 lssnshtgtt sstasscdte ftkedeqrlk dylqglkndr aavkltmlel eslhldplsy
601 dvkprgdsqr ldlenavlmq elmamkeema elkeqlylle kekkalelkl gtreaqeqay
661 lvhlehlkse vseqkeqmmr sisstssgsk dkpgkecada aspalelael rttcsenela
721 aeftnalrre kklkarvqel vsalerltks seirhqqsae fvmdlkrans nlvaayekak
781 kkhqmklkkl esqmmamver hetqvrmlkg rialleeens rphtnetrlk
```

FIG. 7E

```
  1 madvfpgnds tasqdvanrf arkgairqkm vhevkdhkfl arffkqptfc shctdfiwgf
 61 gkqgfgcqvc cfvvhkrcne fvtfscpgad kgpdtddprs khkfkihtyg sptfcdhcgs
121 llyglihqgm kcdtcdmmvh kqcvlnvpsl cgmdhtekrg riylkaevad eklkvtvrda
181 knlipmdpng lsdpyvklkl ipdpkmeskq ktktlrstln pqwnesftfk lkpsdkdrrl
241 sveiwdwdrt tmdfmgsls  fgvselmkmp asgwykllnq eegeyynvpl pegdeegnme
301 lrqkfekakl gpagnkvisp sedrkqpsnn ldrvkltdfn flmvlgkgsf gkvmladrkg
361 teelyaikil kkdvvlqddd vectmvekrv lalldkppfl tqlhscfqtv drlyfvmeyv
421 nggdlmyhiq qvgkfkeppa vfyaaeisig lfflbkrgii yrdlkldnvm ldseghikia
481 dfgmckebmm dgvttrtfcg tpdyiapeii aygppygksvd wwaygvllye mlagqppfdg
541 ededelfqsi mehovsypks iskeavsick glmtkhpakr lgcgpegerd vrehaffrrl
601 dweklenrel qppfkpkvcg kgaenfdkff trgqpvltpp dqlvianidq sdfegfsyvn
661 pqfvhpilq
```

FIG. 7F

```
  1 mdilceents lestcnslmq lnddtrlysn dfnsgearts dafnwtvdse nrtalscegc
 61 ispsclslih lqekmwsall tavviltia gmilvimavs lekklqmatn yflmslaiad
121 mlgflvmpv smltilygyr wplpskicav wlyldvlfst asimhlcais ldryvaiqmp
181 ihnsrfnsrt kaflkilavw tisvglsmpl pvfglqdddsk vfkegsclla ddnfvligsf
241 vsff_pltim vityfltiks lqkeatlcvs dlgtraklas fsflpqssls seklfqrsih
301 repgsytgrr tmgsisneqr ackvlgivff lfvvmwcpff itriravick escnedviga
361 linvfvwigy lssavnplvy fsrylgcqyk enkkplqlil vntipalayk
421 ssqlqmgqkk nskqdakttd ndcsmvalgk qhseeaskdn sdgvmekv__sg_v__
```

FIG. 7G

```
  1 malsyrvsel qstipehiiq stivhvissn wgglqtesip eemkqiveeq gnklhwaall
 61 ilmvilptig gmtlvllavs lekklqyatn yflmelavad llvglfvmpl alltlmfeam
121 wplplvlcpa wlfldvlfst asimhlcais vdryialkkp iganymsra tafikitvvw
181 lisiglaipv plkgletdvd npnmitcvlt kerfgdfmlf gslaafftpl aimvtyflt
241 ihalgkkayl vmkppqqrlt witvstvfqr detpcssspek vamldgsrkd kalpnsgdet
301 lmrrtstigk ksvqtieneq raskvlgivf flfllmwcpf fitnitlvlc dscngttlqm
361 lleifvwigy vsgvnplvy tlfnktfrda fgryitcnyr ackvktlrk rsekiyfrnp
421 maenskffkk hgirmginpa nygspmrlrs stigqsseii ldtllitene gdkteeqvky
481 y
```

FIG. 7H

```
   1 maaasydqli kqvealkmen snlrqeledn snhltklete asnmkevlkq lqgsiedean
  61 assgqidlle rlkelnldss nfpgvklrsk mslrsygere gsvssrsgec spvpngsfpr
 121 rgfvngsres tgyleeleke rslilladldk eekekdwyya qlmlikrid slpltanfsi
 181 qtdmtrrqle yearqirvan eeqigtcqdm ekraqrriar iqqiekdilr irqliqsqat
 241 eaerssqnkh ergshdaerq negqgvgein matsgngqgs ttrmdnetas vlsssstnsa
 301 prrltshlgt kvemvyslis migthdkddm srtliamsss qdscismrqs gelpliiqll
 361 hgndkdsvli gnsrgskear arasaalhni ihsqpddkrg rreirvlhli eqirayceit
 421 wewqeahepg mdqdknpmpa pvehqicpav cvlmklsfde ehrhanmelg glqaisellq
 481 vdcemygltn dhysitlrry agmaltnltf gdvankatlc smkgcmralv aqiksesedi
 541 cqviasvlrn lswradvnsk ktlrevgsvk almecalevk kestlksvls alwnlsahct
 601 enkadicavd galaflvgtl tyrsqtntla iiesgggilr nvssliatne dhrqilrenn
 661 clqtliqhlk shsltivsna cgtlwnlsar npkdqealwd mgavsmlknl ihskhimlam
 721 gsaaairnln anrpakykda nirspgsslp slhvrkqkal eaeldaqhls etfdnidnls
 781 pkashrskqr hkqslygdyv fdtnrhddnr sdnfntgrmt vispylnttv lpssassrqs
 841 ldssrsekdr slerergigl gnyhpatenp grsskrglqi sttaaqiakv neevsaihts
 901 qedrssgstt elhcvtdern alrrssaaht hsntynftks ensnrtcsmp yakleykrss
 961 ndslnsvsss dgygkrgqnk psiesysedd eskfcsygqy padlabkihs arhmddndge
1021 ldtpimyslk ysdeqlnsgr qspsqnerwa rpkhtiedei kqseqrqsrn qsttypvyte
1081 stddkhlkfq phfgqqecvs pyrsrgangs etnrvgsnhg inqnvsqsle qeddyeddkp
1141 tnyserysee eqheeeerpt nysikyneek rhvdqpidys lkyatdipss qkqsfsfsks
1201 ssgqsekteh masssentst passnakrqmq lhpssaqsrs gqpqkaatck vssinqetiq
1261 tycvedtpic fsrcsslssl ssaedeigcn qttqeadsan tlqiaeikek igtrsaedrv
1321 sevpavsqhp rtkssrlqgs slsssesarhk avefssgaks psksgaqtpk sppehyvqet
1381 plmfsrctsv ssldsfesrs iasevqsepc sgmvsgiisp sdlpdspgqt mppsrektpp
1441 pppqtaqtkr evpknkapta ekresqpkqa avnaavqrvq vlpdadtilh fatestpdgf
1501 scsssisals ldepflqkdv elrimppvqe ndngnetase qpkesnenqe keaektidse
1561 kdilddsddd dieileecii samptkssrk akkpaqtask lpppvarkps qlpvyklips
1621 qnrlqpqkhv sftpgdhmpr vycvegtpln fstatsledi tiesppnela agegvrggaq
1681 sgefekrdti ptegrstdea qggktssvti peiddnkaee gdilaecins ampkgkshkp
1741 frvkkimdqv qqasasssap nknqldgkkk kptspvkpip qnteyrtrvr knadsknnln
1801 aervfsdtkd skkqnlknns kdfndklpnn edrvrgsfaf dsphhytpie gtpyctsrnd
1861 slssldfddd dvdlsrekae lrkakenkes eakvtshtel tsnqqeankt qaiakqpinr
1921 gqpkpilqkq stfpqsskdi pdrgaatdek lqnfaientp vcfshnssls slsdidqenn
1981 nkenepiket eppdsqgeps kpqasgyapk sfhvedtpvc fsrnssissi eidseddllq
2041 ecissampkk kkpsrlkgdn ekhsprnngg iigeditldi kdiqrpdseh glspdsanfd
2101 wkaiqegans ivsslhqaaa aaclsrqass dsdsiislks gisigspfhl tpdqeekpft
2161 snkqprilkp gekstletkk ieseskgikg gkkvykslit gkvrsnseis gqmkqplqan
2221 mpsisrgrtm ihipgvrnss sstspvskkg pplktpasks pseggtatts prgakpsvks
2281 elspvarqts qiggsskaps rsgsrdstps tpaqqplsrp iqspgrnsis pgrngisppn
2341 klsqlprtss petasstksg sgkmsytspg rqmsqqnltk qtglsknass iprsesaskq
2401 lnqnnngrga nkkvelsrns stkssgsesd rserpvlvrq stfikeapsp tlrrkleesa
2461 sfeslspssr paspttrsqaq tpvlspslpd nslsthssvq aggwrklppn lsptieyndq
2521 rpakrhdiar shsespsrlp inrsgtwkre hskhssslpr vetwrrtgss ssilsasses
2581 sekaksedek hvnsisgtkq skenqvsakg twrkikenef sptnstsqtv ssgatngaes
2641 ktliyqmapa vsktedvwvr iedcpinnpr sgrsptgntp pvidsvseka npnikdskdn
2701 qakqnvgngs vpnrtvglen rlnsfiqvda pdqkgteikp gqrnpvpvse tnessivert
2761 pfssssssskh sspsgrvaar vtpfnynpsp rkssadstsa rpsqiptpvn nntkkrdskt
2821 dstessgtqs pkrhsqsylv tsr
``` p75NGFR
(Low-affinity nerve growth factor receptor)

FIG. 9

| | C-terminal amino acid sequence |
|---|---|
| Fas | NEIQSLV |
| p75NGFR | STATSPV | t(S/T)-X-V —COOH ↔ PDZ domain interaction

In vitro interaction of 35S-labeled FAP-1 with various receptors
— FAP-1 binds to the cytoplasmic region of p75NGFR.

FIG. 11A

FAP-1 binds to C-terminal three amino acids SPV of p75NGFR.

| p75 deletion mutants | FAP-1 interaction |
|---|---|
| wild type (1–223/244–396) | + |
| 245–396 | − |
| 245–337 | + |
| 302–396 | − |
| 302–337 | + |
| 338–396 | + |
| SPV (394–396) | + |

FIG. 12

FAP-1 binds to p75NGFR C-terminal cytoplasmic region in yeast.

|  | VP16-FAP-1 | VP16-cRaf |
|---|---|---|
| LexA-p75NGFR(338-396) | + | – |
| LexA-p75NGFR(365-396) | + | – |
| LexA-Fas | ++ | – |
| LexA-Ras$^{V12}$ | – | + |
| LexA-Lamin | – | – |

FIG. 13A
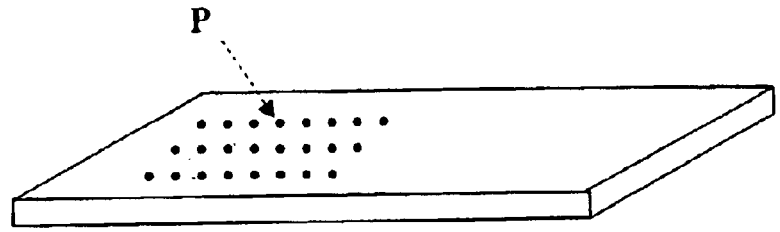
FIG. 13B
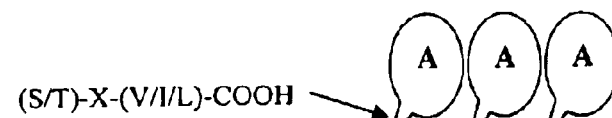
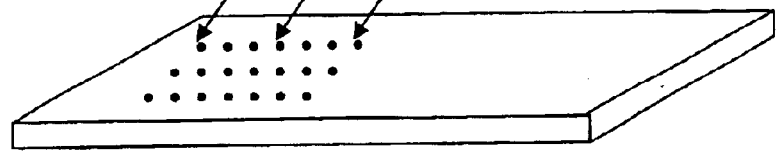
FIG. 13C
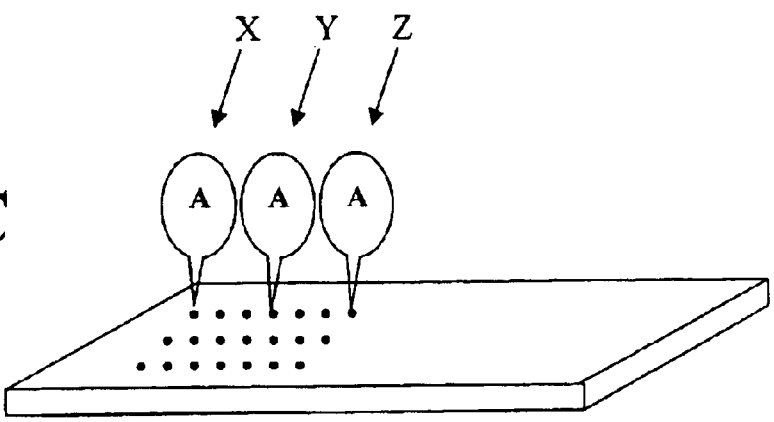

SEQUENCE LISTING

```
<160> NUMBER OF SEQ ID NOS: 34

<210> SEQ ID NO 1
<211> LENGTH: 4
<212> TYPE: PRT
<213> ORGANISM: Artificial Sequence
<220> FEATURE:
<223> OTHER INFORMATION: Description of Artificial
      Sequence:source:synthesized
<220> FEATURE:
<221> NAME/KEY: SITE
<222> LOCATION: (1)
<223> OTHER INFORMATION: Xaa=Gly, Ser, Ala or Glu
<220> FEATURE:
<221> NAME/KEY: SITE
<222> LOCATION: (4)
<223> OTHER INFORMATION: Xaa=Phe, Ile or Leu

<400> SEQUENCE: 1

Xaa Leu Gly Xaa
  1

<210> SEQ ID NO 2
<211> LENGTH: 9
<212> TYPE: PRT
<213> ORGANISM: Artificial Sequence
<220> FEATURE:
<223> OTHER INFORMATION: Description of Artificial
      Sequence:source:synthesized
<220> FEATURE:
<221> NAME/KEY: SITE
<222> LOCATION: (1)
<223> OTHER INFORMATION: Xaa=Lys, Arg or Gln
<220> FEATURE:
<221> NAME/KEY: SITE
<222> LOCATION: (2)..(5)
<223> OTHER INFORMATION: Xaa=any amino acid, up to 2 Xaa may be missing
<220> FEATURE:
```

```
<221> NAME/KEY: SITE
<222> LOCATION: (6)
<223> OTHER INFORMATION: Xaa=Gly, Ser, Ala or Glu
<220> FEATURE:
<221> NAME/KEY: SITE
<222> LOCATION: (9)
<223> OTHER INFORMATION: Xaa=Phe, Ile or Leu

<400> SEQUENCE: 2

Xaa Xaa Xaa Xaa Xaa Xaa Leu Gly Xaa
  1               5

<210> SEQ ID NO 3
<211> LENGTH: 4
<212> TYPE: PRT
<213> ORGANISM: Artificial Sequence
<220> FEATURE:
<223> OTHER INFORMATION: Description of Artificial
      Sequence:source:synthesized

<400> SEQUENCE: 3

Ser Leu Gly Ile
  1

<210> SEQ ID NO 4
<211> LENGTH: 3
<212> TYPE: PRT
<213> ORGANISM: Artificial Sequence
<220> FEATURE:
<223> OTHER INFORMATION: Description of Artificial
      Sequence:source:synthesized
<220> FEATURE:
<221> NAME/KEY: SITE
<222> LOCATION: (1)
<223> OTHER INFORMATION: Xaa=Ser or Thr
<220> FEATURE:
<221> NAME/KEY: SITE
<222> LOCATION: (2)
<223> OTHER INFORMATION: Xaa=any one amino acid
<220> FEATURE:
<221> NAME/KEY: SITE
<222> LOCATION: (3)
<223> OTHER INFORMATION: Xaa=Val, Ile or Leu

<400> SEQUENCE: 4

Xaa Xaa Xaa
  1

<210> SEQ ID NO 5
<211> LENGTH: 15
<212> TYPE: PRT
<213> ORGANISM: human

<400> SEQUENCE: 5

Asp Ser Glu Asn Ser Asn Phe Arg Asn Glu Ile Gln Ser Leu Val
  1               5                  10                  15

<210> SEQ ID NO 6
<211> LENGTH: 15
<212> TYPE: PRT
<213> ORGANISM: rat

<400> SEQUENCE: 6

Ser Ile Ser Asn Ser Arg Asn Glu Asn Glu Gly Gln Ser Leu Glu
  1               5                  10                  15

<210> SEQ ID NO 7
<211> LENGTH: 15
<212> TYPE: PRT
```

```
<213> ORGANISM: mouse

<400> SEQUENCE: 7

Ser Thr Pro Asp Thr Gly Asn Glu Asn Glu Gly Gln Cys Leu Glu
 1               5                  10                  15

<210> SEQ ID NO 8
<211> LENGTH: 4
<212> TYPE: PRT
<213> ORGANISM: Artificial Sequence
<220> FEATURE:
<223> OTHER INFORMATION: Description of Artificial
      Sequence:source:synthesized

<400> SEQUENCE: 8

Glu Ser Leu Val
 1

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence:
      source:synthesized

<400> SEQUENCE: 9

Thr Ile Gln Ser Val Ile
 1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial
      Sequence:source:synthesized

<400> SEQUENCE: 10

Arg Gly Phe Ile Ser Ser Leu Val
 1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial
      Sequence:source:synthesized

<400> SEQUENCE: 11

Arg Glu Thr Ile Glu Ser Thr Val
 1               5

<210> SEQ ID NO 12
<211> LENGTH: 11
<212> TYPE: PRT
<213> ORGANISM: Artificial Sequence
<220> FEATURE:
<223> OTHER INFORMATION: Description of Artificial
      Sequence:source:synthesized

<400> SEQUENCE: 12

Gln Asn Phe Arg Thr Tyr Ile Val Ser Phe Val
 1               5                  10

<210> SEQ ID NO 13
```

```
<211> LENGTH: 13
<212> TYPE: PRT
<213> ORGANISM: Artificial Sequence
<220> FEATURE:
<223> OTHER INFORMATION: Description of Artificial
      Sequence:source:synthesized

<400> SEQUENCE: 13

Ser Asp Ser Asn Met Asn Met Asn Glu Leu Ser Glu Val
 1               5                  10

<210> SEQ ID NO 14
<211> LENGTH: 15
<212> TYPE: PRT
<213> ORGANISM: Artificial Sequence
<220> FEATURE:
<223> OTHER INFORMATION: Description of Artificial
      Sequence:source:synthesized

<400> SEQUENCE: 14

Pro Pro Thr Cys Ser Gln Ala Asn Ser Gly Arg Ile Ser Thr Leu
 1               5                  10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial
      Sequence:source:synthesized

<400> SEQUENCE: 15

Ile Asp Leu Ala Ser Glu Phe Leu Phe Leu Ser Asn Ser Phe Leu
 1               5                  10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial
      Sequence:source:synthesized

<400> SEQUENCE: 16

Asp Ser Glu Met Tyr Asn Phe Arg Ser Gln Leu Ala Ser Val Val
 1               5                  10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial
      Sequence:source:synthesized

<400> SEQUENCE: 17

Ile Pro Pro Asp Ser Glu Asp Gly Asn Glu Glu Gln Ser Leu Val
 1               5                  10                  15

<210> SEQ ID NO 18
<211> LENGTH: 4
<212> TYPE: PRT
<213> ORGANISM: Artificial Sequence
<220> FEATURE:
<223> OTHER INFORMATION: Description of Artificial
      Sequence:source:synthesized

<400> SEQUENCE: 18
```

```
Gln Ser Leu Val
  1

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence:source
      synthesized

<400> SEQUENCE: 19

Ile Gln Ser Leu Val
  1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial
      Sequence:source:synthesized

<400> SEQUENCE: 20

Glu Ile Gln Ser Leu Val
  1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial
      Sequence:source:synthesized

<400> SEQUENCE: 21

Asn Glu Ile Gln Ser Leu Val
  1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial
      Sequence:source:synthesized

<400> SEQUENCE: 22

Arg Asn Glu Ile Gln Ser Leu Val
  1               5

<210> SEQ ID NO 23
<211> LENGTH: 15
<212> TYPE: PRT
<213> ORGANISM: Artificial Sequence
<220> FEATURE:
<223> OTHER INFORMATION: Description of Artificial
      Sequence:source:synthesized

<400> SEQUENCE: 23

Asp Ser Glu Asn Ser Asn Phe Arg Asn Glu Ile Gln Ser Leu Val
  1               5                  10                  15

<210> SEQ ID NO 24
<211> LENGTH: 427
<212> TYPE: PRT
<213> ORGANISM: human
```

```
<400> SEQUENCE: 24

Met Gly Ala Gly Ala Thr Gly Arg Ala Met Asp Gly Pro Arg Leu Leu
 1               5                  10                  15

Leu Leu Leu Leu Leu Gly Val Ser Leu Gly Ala Lys Glu Ala Cys
            20                  25                  30

Pro Thr Gly Leu Tyr Thr His Ser Gly Glu Cys Cys Lys Ala Cys Asn
        35                  40                  45

Leu Gly Glu Gly Val Ala Gln Pro Cys Gly Ala Asn Gln Thr Val Cys
    50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
            100                 105                 110

Tyr Tyr Gln Asp Glu Thr Thr Gly Arg Cys Glu Ala Cys Arg Val Cys
        115                 120                 125

Glu Ala Gly Ser Gly Leu Val Phe Ser Cys Gln Asp Lys Gln Asn Thr
    130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
        195                 200                 205

Ala Pro Ser Thr Gln Glu Pro Glu Ala Pro Pro Glu Gln Asp Leu Ile
    210                 215                 220

Ala Ser Thr Val Ala Gly Val Val Thr Thr Val Met Gly Ser Ser Gln
225                 230                 235                 240

Pro Val Val Thr Arg Gly Thr Thr Asp Asn Leu Ile Pro Val Tyr Cys
                245                 250                 255

Ser Ile Leu Ala Ala Val Val Val Gly Leu Val Ala Tyr Ile Ala Phe
            260                 265                 270

Lys Arg Trp Asn Ser Cys Lys Gln Asn Lys Gly Gly Ala Asn Ser Arg
        275                 280                 285

Pro Val Asn Gln Thr Pro Pro Pro Glu Gly Glu Lys Ile His Ser Asp
    290                 295                 300

Ser Gly Ile Ser Val Asp Ser Gln Ser Leu His Asp Gln Gln Pro His
305                 310                 315                 320

Thr Gln Thr Ala Ser Gly Gln Ala Leu Lys Gly Asp Gly Gly Leu Tyr
                325                 330                 335

Ser Ser Leu Pro Pro Ala Lys Arg Glu Glu Val Glu Lys Leu Leu Asn
            340                 345                 350

Gly Ser Ala Gly Asp Thr Trp Arg His Leu Ala Gly Glu Leu Gly Tyr
        355                 360                 365

Gln Pro Glu His Ile Asp Ser Phe Thr His Glu Ala Cys Pro Val Arg
    370                 375                 380

Ala Leu Leu Ala Ser Trp Ala Thr Gln Asp Ser Ala Thr Leu Asp Ala
385                 390                 395                 400

Leu Leu Ala Ala Leu Arg Arg Ile Gln Arg Ala Asp Leu Val Glu Ser
                405                 410                 415
```

```
Leu Cys Ser Glu Ser Thr Ala Thr Ser Pro Val
            420                 425

<210> SEQ ID NO 25
<211> LENGTH: 458
<212> TYPE: PRT
<213> ORGANISM: human

<400> SEQUENCE: 25

Met Asn Arg Gly Val Pro Phe Arg His Leu Leu Leu Val Leu Gln Leu
 1               5                  10                  15

Ala Leu Leu Pro Ala Ala Thr Gln Gly Lys Lys Val Val Leu Gly Lys
                20                  25                  30

Lys Gly Asp Thr Val Glu Leu Thr Cys Thr Ala Ser Gln Lys Lys Ser
            35                  40                  45

Ile Gln Phe His Trp Lys Asn Ser Asn Gln Ile Lys Ile Leu Gly Asn
        50                  55                  60

Gln Gly Ser Phe Leu Thr Lys Gly Pro Ser Lys Leu Asn Asp Arg Ala
 65                  70                  75                  80

Asp Ser Arg Arg Ser Leu Trp Asp Gln Gly Asn Phe Pro Leu Ile Ile
                    85                  90                  95

Lys Asn Leu Lys Ile Glu Asp Ser Asp Thr Tyr Ile Cys Glu Val Glu
                100                 105                 110

Asp Gln Lys Glu Glu Val Gln Leu Leu Val Phe Gly Leu Thr Ala Asn
            115                 120                 125

Ser Asp Thr His Leu Leu Gln Gly Gln Ser Leu Thr Ile Thr Leu Glu
        130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
        210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
                260                 265                 270

Gln Met Gly Lys Lys Leu Pro Leu His Leu Thr Leu Pro Gln Ala Leu
            275                 280                 285

Pro Gln Tyr Ala Gly Ser Gly Asn Leu Thr Leu Ala Leu Glu Ala Lys
        290                 295                 300

Thr Gly Lys Leu His Gln Glu Asn Val Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
                340                 345                 350

Lys Arg Glu Lys Ala Val Trp Val Leu Asn Pro Glu Ala Gly Met Trp
```

```
            355                 360                 365
Gln Cys Leu Leu Ser Asp Ser Gly Gln Val Leu Leu Glu Ser Asn Ile
    370                 375                 380
Lys Val Leu Pro Thr Trp Ser Thr Pro Val Gln Pro Met Ala Leu Ile
385                 390                 395                 400
Val Leu Gly Gly Val Ala Gly Leu Leu Leu Phe Ile Gly Leu Gly Ile
                405                 410                 415
Phe Phe Cys Val Arg Cys Arg His Arg Arg Gln Ala Glu Arg Met
                420                 425                 430
Ser Gln Ile Lys Arg Leu Leu Ser Glu Lys Lys Glu Cys Gln Cys Pro
                435                 440                 445
His Arg Phe Gln Lys Thr Cys Ser Pro Ile
        450                 455

<210> SEQ ID NO 26
<211> LENGTH: 828
<212> TYPE: PRT
<213> ORGANISM: human

<400> SEQUENCE: 26

Met Asn Ser Gly Val Ala Met Lys Tyr Gly Asn Asp Ser Ser Ala Glu
1               5                   10                  15
Leu Ser Glu Leu His Ser Ala Ala Leu Ala Ser Leu Lys Gly Asp Ile
                20                  25                  30
Val Glu Leu Asn Lys Arg Leu Gln Gln Thr Glu Arg Glu Asp Leu Leu
            35                  40                  45
Glu Lys Lys Leu Ala Lys Ala Gln Cys Glu Gln Ser His Leu Met Arg
    50                  55                  60
Glu His Glu Asp Val Gln Glu Arg Thr Thr Leu Arg Tyr Glu Glu Arg
65                  70                  75                  80
Ile Thr Glu Leu His Ser Val Ile Ala Glu Leu Asn Lys Lys Ile Asp
                85                  90                  95
Arg Leu Gln Gly Thr Thr Ile Arg Glu Glu Asp Glu Tyr Ser Glu Leu
                100                 105                 110
Arg Ser Glu Leu Ser Gln Ser Gln His Glu Val Asn Glu Asp Ser Arg
            115                 120                 125
Ser Met Asp Gln Asp Gln Thr Ser Val Ser Ile Pro Glu Asn Gln Ser
130                 135                 140
Thr Met Val Thr Ala Asp Met Asp Asn Cys Ser Asp Ile Asn Ser Glu
145                 150                 155                 160
Leu Gln Arg Val Leu Thr Gly Leu Glu Asn Val Val Cys Gly Arg Lys
                165                 170                 175
Lys Ser Ser Cys Ser Leu Ser Val Ala Glu Val Asp Arg His Ile Glu
                180                 185                 190
Gln Leu Thr Thr Ala Ser Glu His Cys Asp Leu Ala Ile Lys Thr Val
            195                 200                 205
Glu Glu Ile Glu Gly Val Leu Gly Arg Asp Leu Tyr Pro Asn Leu Ala
    210                 215                 220
Glu Glu Arg Ser Arg Trp Glu Lys Glu Leu Ala Gly Leu Arg Glu Glu
225                 230                 235                 240
Asn Glu Ser Leu Thr Ala Met Leu Cys Ser Lys Glu Glu Glu Leu Asn
                245                 250                 255
Arg Thr Lys Ala Thr Met Asn Ala Ile Arg Glu Glu Arg Asp Arg Leu
                260                 265                 270
```

```
Arg Arg Arg Val Arg Glu Leu Gln Thr Arg Leu Gln Ser Val Gln Ala
        275                 280                 285

Thr Gly Pro Ser Ser Pro Gly Arg Leu Thr Ser Thr Asn Arg Pro Ile
        290                 295                 300

Asn Pro Ser Thr Gly Glu Leu Ser Thr Ser Ser Ser Ser Asn Asp Ile
305                 310                 315                 320

Pro Ile Ala Lys Ile Ala Glu Arg Val Lys Leu Ser Lys Thr Arg Ser
                325                 330                 335

Glu Ser Ser Ser Asp Arg Pro Val Leu Gly Ser Glu Ile Ser Ser
            340                 345                 350

Ile Gly Val Ser Ser Ser Val Ala Glu His Leu Ala His Ser Leu Gln
            355                 360                 365

Asp Cys Ser Asn Ile Gln Glu Ile Phe Gln Thr Leu Tyr Ser His Gly
    370                 375                 380

Ser Ala Ile Ser Glu Ser Lys Ile Arg Glu Phe Glu Val Glu Thr Glu
385                 390                 395                 400

Arg Leu Asn Ser Arg Ile Glu His Leu Lys Ser Gln Asn Asp Leu Leu
                405                 410                 415

Thr Ile Thr Leu Glu Glu Cys Lys Ser Asn Ala Glu Arg Met Ser Met
            420                 425                 430

Leu Val Gly Lys Tyr Glu Ser Asn Ala Thr Ala Leu Arg Leu Ala Leu
            435                 440                 445

Gln Tyr Ser Glu Gln Cys Ile Glu Ala Tyr Glu Leu Leu Leu Ala Leu
    450                 455                 460

Ala Glu Ser Glu Gln Ser Leu Ile Leu Gly Gln Phe Arg Ala Ala Gly
465                 470                 475                 480

Val Gly Ser Ser Pro Gly Asp Gln Ser Gly Asp Glu Asn Ile Thr Gln
                485                 490                 495

Met Leu Lys Arg Ala His Asp Cys Arg Lys Thr Ala Glu Asn Ala Ala
            500                 505                 510

Lys Ala Leu Leu Met Lys Leu Asp Gly Ser Cys Gly Gly Ala Phe Ala
            515                 520                 525

Val Ala Gly Cys Ser Val Gln Pro Trp Glu Ser Leu Ser Ser Asn Ser
    530                 535                 540

His Thr Ser Thr Thr Ser Ser Thr Ala Ser Ser Cys Asp Thr Glu Phe
545                 550                 555                 560

Thr Lys Glu Asp Glu Gln Arg Leu Lys Asp Tyr Ile Gln Gln Leu Lys
                565                 570                 575

Asn Asp Arg Ala Ala Val Lys Leu Thr Met Leu Glu Leu Glu Ser Ile
            580                 585                 590

His Ile Asp Pro Leu Ser Tyr Asp Val Lys Pro Arg Gly Asp Ser Gln
            595                 600                 605

Arg Leu Asp Leu Glu Asn Ala Val Leu Met Gln Glu Leu Met Ala Met
    610                 615                 620

Lys Glu Glu Met Ala Glu Leu Lys Ala Gln Leu Tyr Leu Leu Glu Lys
625                 630                 635                 640

Glu Lys Lys Ala Leu Glu Leu Lys Leu Ser Thr Arg Glu Ala Gln Glu
                645                 650                 655

Gln Ala Tyr Leu Val His Ile Glu His Leu Lys Ser Glu Val Glu Glu
            660                 665                 670

Gln Lys Glu Gln Arg Met Arg Ser Leu Ser Ser Thr Ser Ser Gly Ser
            675                 680                 685

Lys Asp Lys Pro Gly Lys Glu Cys Ala Asp Ala Ala Ser Pro Ala Leu
```

```
            690                 695                 700
Ser Leu Ala Glu Leu Arg Thr Thr Cys Ser Glu Asn Glu Leu Ala Ala
705                 710                 715                 720

Glu Phe Thr Asn Ala Ile Arg Arg Glu Lys Lys Leu Lys Ala Arg Val
                725                 730                 735

Gln Glu Leu Val Ser Ala Leu Glu Arg Leu Thr Lys Ser Ser Glu Ile
                740                 745                 750

Arg His Gln Gln Ser Ala Glu Phe Val Asn Asp Leu Lys Arg Ala Asn
                755                 760                 765

Ser Asn Leu Val Ala Ala Tyr Glu Lys Ala Lys Lys His Gln Asn
                770                 775                 780

Lys Leu Lys Lys Leu Glu Ser Gln Met Met Ala Met Val Glu Arg His
785                 790                 795                 800

Glu Thr Gln Val Arg Met Leu Lys Gln Arg Ile Ala Leu Leu Glu Glu
                805                 810                 815

Glu Asn Ser Arg Pro His Thr Asn Glu Thr Ser Leu
                820                 825

<210> SEQ ID NO 27
<211> LENGTH: 672
<212> TYPE: PRT
<213> ORGANISM: human

<400> SEQUENCE: 27

Met Ala Asp Val Phe Pro Gly Asn Asp Ser Thr Ala Ser Gln Asp Val
1               5                   10                  15

Ala Asn Arg Phe Ala Arg Lys Gly Ala Leu Arg Gln Lys Asn Val His
                20                  25                  30

Glu Val Lys Asp His Lys Phe Ile Ala Arg Phe Phe Lys Gln Pro Thr
                35                  40                  45

Phe Cys Ser His Cys Thr Asp Phe Ile Trp Gly Phe Gly Lys Gly Gly
    50                  55                  60

Phe Gln Cys Gln Val Cys Cys Phe Val Val His Lys Arg Cys His Glu
65                  70                  75                  80

Phe Val Thr Phe Ser Cys Pro Gly Ala Asp Lys Gly Pro Asp Thr Asp
                85                  90                  95

Asp Pro Arg Ser Lys His Lys Phe Lys Ile His Thr Tyr Gly Ser Pro
                100                 105                 110

Thr Phe Cys Asp His Cys Gly Ser Leu Leu Tyr Gly Leu Ile His Gln
            115                 120                 125

Gly Met Lys Cys Asp Thr Cys Asp Met Asn Val His Lys Gln Cys Val
130                 135                 140

Ile Asn Val Pro Ser Leu Cys Gly Met Asp His Thr Glu Lys Arg Gly
145                 150                 155                 160

Arg Ile Tyr Leu Lys Ala Glu Val Ala Asp Glu Lys Leu His Val Thr
                165                 170                 175

Val Arg Asp Ala Lys Asn Leu Ile Pro Met Asp Pro Asn Gly Leu Ser
                180                 185                 190

Asp Pro Tyr Val Lys Leu Lys Leu Ile Pro Asp Pro Lys Asn Glu Ser
                195                 200                 205

Lys Gln Lys Thr Lys Thr Ile Arg Ser Thr Leu Asn Pro Gln Trp Asn
                210                 215                 220

Glu Ser Phe Thr Phe Lys Leu Lys Pro Ser Asp Lys Asp Arg Arg Leu
225                 230                 235                 240
```

-continued

```
Ser Val Glu Ile Trp Asp Trp Asp Arg Thr Thr Arg Asn Asp Phe Met
            245                 250                 255

Gly Ser Leu Ser Phe Gly Val Ser Glu Leu Met Lys Met Pro Ala Ser
            260                 265                 270

Gly Trp Tyr Lys Leu Leu Asn Gln Glu Glu Gly Glu Tyr Tyr Asn Val
            275                 280                 285

Pro Ile Pro Glu Gly Asp Glu Glu Gly Asn Met Glu Leu Arg Gln Lys
290                 295                 300

Phe Glu Lys Ala Lys Leu Gly Pro Ala Gly Asn Lys Val Ile Ser Pro
305                 310                 315                 320

Ser Glu Asp Arg Lys Gln Pro Ser Asn Asn Leu Asp Arg Val Lys Leu
            325                 330                 335

Thr Asp Phe Asn Phe Leu Met Val Leu Gly Lys Gly Ser Phe Gly Lys
            340                 345                 350

Val Met Leu Ala Asp Arg Lys Gly Thr Glu Glu Leu Tyr Ala Ile Lys
            355                 360                 365

Ile Leu Lys Lys Asp Val Val Ile Gln Asp Asp Val Glu Cys Thr
370                 375                 380

Met Val Glu Lys Arg Val Leu Ala Leu Leu Asp Lys Pro Pro Phe Leu
385                 390                 395                 400

Thr Gln Leu His Ser Cys Phe Gln Thr Val Asp Arg Leu Tyr Phe Val
            405                 410                 415

Met Glu Tyr Val Asn Gly Gly Asp Leu Met Tyr His Ile Gln Gln Val
            420                 425                 430

Gly Lys Phe Lys Glu Pro Gln Ala Val Phe Tyr Ala Ala Glu Ile Ser
            435                 440                 445

Ile Gly Leu Phe Phe Leu His Lys Arg Gly Ile Ile Tyr Arg Asp Leu
            450                 455                 460

Lys Leu Asp Asn Val Met Leu Asp Ser Glu Gly His Ile Lys Ile Ala
465                 470                 475                 480

Asp Phe Gly Met Cys Lys Glu His Met Met Asp Gly Val Thr Thr Arg
            485                 490                 495

Thr Phe Cys Gly Thr Pro Asp Tyr Ile Ala Pro Glu Ile Ile Ala Tyr
            500                 505                 510

Gln Pro Tyr Gly Lys Ser Val Asp Trp Trp Ala Tyr Gly Val Leu Leu
            515                 520                 525

Tyr Glu Met Leu Ala Gly Gln Pro Pro Phe Asp Gly Glu Asp Glu Asp
530                 535                 540

Glu Leu Phe Gln Ser Ile Met Glu His Asn Val Ser Tyr Pro Lys Ser
545                 550                 555                 560

Leu Ser Lys Glu Ala Val Ser Ile Cys Lys Gly Leu Met Thr Lys His
            565                 570                 575

Pro Ala Lys Arg Leu Gly Cys Gly Pro Glu Gly Glu Arg Asp Val Arg
            580                 585                 590

Glu His Ala Phe Phe Arg Arg Ile Asp Trp Glu Lys Leu Glu Asn Arg
            595                 600                 605

Glu Ile Gln Pro Pro Phe Lys Pro Lys Val Cys Gly Lys Gly Ala Glu
            610                 615                 620

Asn Phe Asp Lys Phe Phe Thr Arg Gly Gln Pro Val Leu Thr Pro Pro
625                 630                 635                 640

Asp Gln Leu Val Ile Ala Asn Ile Asp Gln Ser Asp Phe Glu Gly Phe
            645                 650                 655

Ser Tyr Val Asn Pro Gln Phe Val His Pro Ile Leu Gln Ser Ala Val
```

<210> SEQ ID NO 28
<211> LENGTH: 471
<212> TYPE: PRT
<213> ORGANISM: human

<400> SEQUENCE: 28

```
Met Asp Ile Leu Cys Glu Glu Asn Thr Ser Leu Ser Ser Thr Thr Asn
 1               5                  10                  15
Ser Leu Met Gln Leu Asn Asp Asp Thr Arg Leu Tyr Ser Asn Asp Phe
            20                  25                  30
Asn Ser Gly Glu Ala Asn Thr Ser Asp Ala Phe Asn Trp Thr Val Asp
        35                  40                  45
Ser Glu Asn Arg Thr Asn Leu Ser Cys Glu Gly Cys Leu Ser Pro Ser
    50                  55                  60
Cys Leu Ser Leu Leu His Leu Gln Glu Lys Asn Trp Ser Ala Leu Leu
65                  70                  75                  80
Thr Ala Val Val Ile Ile Leu Thr Ile Ala Gly Asn Ile Leu Val Ile
                85                  90                  95
Met Ala Val Ser Leu Glu Lys Lys Leu Gln Asn Ala Thr Asn Tyr Phe
            100                 105                 110
Leu Met Ser Leu Ala Ile Ala Asp Met Leu Leu Gly Phe Leu Val Met
        115                 120                 125
Pro Val Ser Met Leu Thr Ile Leu Tyr Gly Tyr Arg Trp Pro Leu Pro
    130                 135                 140
Ser Lys Leu Cys Ala Val Trp Ile Tyr Leu Asp Val Leu Phe Ser Thr
145                 150                 155                 160
Ala Ser Ile Met His Leu Cys Ala Ile Ser Leu Asp Arg Tyr Val Ala
                165                 170                 175
Ile Gln Asn Pro Ile His His Ser Arg Phe Asn Ser Arg Thr Lys Ala
            180                 185                 190
Phe Leu Lys Ile Ile Ala Val Trp Thr Ile Ser Val Gly Ile Ser Met
        195                 200                 205
Pro Ile Pro Val Phe Gly Leu Gln Asp Asp Ser Lys Val Phe Lys Glu
    210                 215                 220
Gly Ser Cys Leu Leu Ala Asp Asp Asn Phe Val Leu Ile Gly Ser Phe
225                 230                 235                 240
Val Ser Phe Phe Ile Pro Leu Thr Ile Met Val Ile Thr Tyr Phe Leu
                245                 250                 255
Thr Ile Lys Ser Leu Gln Lys Glu Ala Thr Leu Cys Val Ser Asp Leu
            260                 265                 270
Gly Thr Arg Ala Lys Leu Ala Ser Phe Ser Phe Leu Pro Gln Ser Ser
        275                 280                 285
Leu Ser Ser Glu Lys Leu Phe Gln Arg Ser Ile His Arg Glu Pro Gly
    290                 295                 300
Ser Tyr Thr Gly Arg Arg Thr Met Gln Ser Ile Ser Asn Glu Gln Lys
305                 310                 315                 320
Ala Cys Lys Val Leu Gly Ile Val Phe Phe Leu Phe Val Val Met Trp
                325                 330                 335
Cys Pro Phe Phe Ile Thr Asn Ile Met Ala Val Ile Cys Lys Glu Ser
            340                 345                 350
Cys Asn Glu Asp Val Ile Gly Ala Leu Leu Asn Val Phe Val Trp Ile
        355                 360                 365
```

```
Gly Tyr Leu Ser Ser Ala Val Asn Pro Leu Val Tyr Thr Leu Phe Asn
    370                 375                 380

Lys Thr Tyr Arg Ser Ala Phe Ser Arg Tyr Ile Gln Cys Gln Tyr Lys
385                 390                 395                 400

Glu Asn Lys Lys Pro Leu Gln Leu Ile Leu Val Asn Thr Ile Pro Ala
                405                 410                 415

Leu Ala Tyr Lys Ser Ser Gln Leu Gln Met Gly Gln Lys Lys Asn Ser
            420                 425                 430

Lys Gln Asp Ala Lys Thr Thr Asp Asn Asp Cys Ser Met Val Ala Leu
        435                 440                 445

Gly Lys Gln His Ser Glu Glu Ala Ser Lys Asp Asn Ser Asp Gly Val
    450                 455                 460

Asn Glu Lys Val Ser Cys Val
465                 470

<210> SEQ ID NO 29
<211> LENGTH: 481
<212> TYPE: PRT
<213> ORGANISM: human

<400> SEQUENCE: 29

Met Ala Leu Ser Tyr Arg Val Ser Glu Leu Gln Ser Thr Ile Pro Glu
1               5                   10                  15

His Ile Leu Gln Ser Thr Phe Val His Val Ile Ser Ser Asn Trp Ser
            20                  25                  30

Gly Leu Gln Thr Glu Ser Ile Pro Glu Glu Met Lys Gln Ile Val Glu
        35                  40                  45

Glu Gln Gly Asn Lys Leu His Trp Ala Ala Leu Leu Ile Leu Met Val
    50                  55                  60

Ile Ile Pro Thr Ile Gly Gly Asn Thr Leu Val Ile Leu Ala Val Ser
65                  70                  75                  80

Leu Glu Lys Lys Leu Gln Tyr Ala Thr Asn Tyr Phe Leu Met Ser Leu
                85                  90                  95

Ala Val Ala Asp Leu Leu Val Gly Leu Phe Val Met Pro Ile Ala Leu
            100                 105                 110

Leu Thr Ile Met Phe Glu Ala Met Trp Pro Leu Pro Leu Val Leu Cys
        115                 120                 125

Pro Ala Trp Leu Phe Leu Asp Val Leu Phe Ser Thr Ala Ser Ile Met
130                 135                 140

His Leu Cys Ala Ile Ser Val Asp Arg Tyr Ile Ala Ile Lys Lys Pro
145                 150                 155                 160

Ile Gln Ala Asn Gln Tyr Asn Ser Arg Ala Thr Ala Phe Ile Lys Ile
                165                 170                 175

Thr Val Val Trp Leu Ile Ser Ile Gly Ile Ala Ile Pro Val Pro Ile
            180                 185                 190

Lys Gly Ile Glu Thr Asp Val Asp Asn Pro Asn Asn Ile Thr Cys Val
        195                 200                 205

Leu Thr Lys Glu Arg Phe Gly Asp Phe Met Leu Phe Gly Ser Leu Ala
    210                 215                 220

Ala Phe Phe Thr Pro Leu Ala Ile Met Ile Val Thr Tyr Phe Leu Thr
225                 230                 235                 240

Ile His Ala Leu Gln Lys Lys Ala Tyr Leu Val Lys Asn Lys Pro Pro
                245                 250                 255

Gln Arg Leu Thr Trp Leu Thr Val Ser Thr Val Phe Gln Arg Asp Glu
            260                 265                 270
```

```
Thr Pro Cys Ser Ser Pro Glu Lys Val Ala Met Leu Asp Gly Ser Arg
            275                 280                 285
Lys Asp Lys Ala Leu Pro Asn Ser Gly Asp Glu Thr Leu Met Arg Arg
        290                 295                 300
Thr Ser Thr Ile Gly Lys Lys Ser Val Gln Thr Ile Ser Asn Glu Gln
305                 310                 315                 320
Arg Ala Ser Lys Val Leu Gly Ile Val Phe Leu Phe Leu Leu Met
                325                 330                 335
Trp Cys Pro Phe Phe Ile Thr Asn Ile Thr Leu Val Leu Cys Asp Ser
                340                 345                 350
Cys Asn Gln Thr Thr Leu Gln Met Leu Leu Glu Ile Phe Val Trp Ile
            355                 360                 365
Gly Tyr Val Ser Ser Gly Val Asn Pro Leu Val Tyr Thr Leu Phe Asn
        370                 375                 380
Lys Thr Phe Arg Asp Ala Phe Gly Arg Tyr Ile Thr Cys Asn Tyr Arg
385                 390                 395                 400
Ala Thr Lys Ser Val Lys Thr Leu Arg Lys Arg Ser Ser Lys Ile Tyr
                405                 410                 415
Phe Arg Asn Pro Met Ala Glu Asn Ser Lys Phe Phe Lys Lys His Gly
                420                 425                 430
Ile Arg Asn Gly Ile Asn Pro Ala Met Tyr Gln Ser Pro Met Arg Leu
            435                 440                 445
Arg Ser Ser Thr Ile Gln Ser Ser Ser Ile Ile Leu Leu Asp Thr Leu
        450                 455                 460
Leu Leu Thr Glu Asn Glu Gly Asp Lys Thr Glu Glu Gln Val Ser Tyr
465                 470                 475                 480
Val

<210> SEQ ID NO 30
<211> LENGTH: 2843
<212> TYPE: PRT
<213> ORGANISM: human

<400> SEQUENCE: 30

Met Ala Ala Ala Ser Tyr Asp Gln Leu Leu Lys Gln Val Glu Ala Leu
1               5                   10                  15
Lys Met Glu Asn Ser Asn Leu Arg Gln Glu Leu Glu Asp Asn Ser Asn
            20                  25                  30
His Leu Thr Lys Leu Glu Thr Glu Ala Ser Asn Met Lys Glu Val Leu
        35                  40                  45
Lys Gln Leu Gln Gly Ser Ile Glu Asp Glu Ala Met Ala Ser Ser Gly
    50                  55                  60
Gln Ile Asp Leu Leu Glu Arg Leu Lys Glu Leu Asn Leu Asp Ser Ser
65                  70                  75                  80
Asn Phe Pro Gly Val Lys Leu Arg Ser Lys Met Ser Leu Arg Ser Tyr
                85                  90                  95
Gly Ser Arg Glu Gly Ser Val Ser Ser Arg Ser Gly Glu Cys Ser Pro
            100                 105                 110
Val Pro Met Gly Ser Phe Pro Arg Arg Gly Phe Val Asn Gly Ser Arg
        115                 120                 125
Glu Ser Thr Gly Tyr Leu Glu Glu Leu Glu Lys Glu Arg Ser Leu Leu
    130                 135                 140
Leu Ala Asp Leu Asp Lys Glu Glu Lys Glu Lys Asp Trp Tyr Tyr Ala
145                 150                 155                 160
```

```
Gln Leu Gln Asn Leu Thr Lys Arg Ile Asp Ser Leu Pro Leu Thr Glu
            165                 170                 175
Asn Phe Ser Leu Gln Thr Asp Met Thr Arg Arg Gln Leu Glu Tyr Glu
            180                 185                 190
Ala Arg Gln Ile Arg Val Ala Met Glu Glu Gln Leu Gly Thr Cys Gln
            195                 200                 205
Asp Met Glu Lys Arg Ala Gln Arg Arg Ile Ala Arg Ile Gln Gln Ile
            210                 215                 220
Glu Lys Asp Ile Leu Arg Ile Arg Gln Leu Leu Gln Ser Gln Ala Thr
225                 230                 235                 240
Glu Ala Glu Arg Ser Ser Gln Asn Lys His Glu Thr Gly Ser His Asp
            245                 250                 255
Ala Glu Arg Gln Asn Glu Gly Gln Gly Val Gly Glu Ile Asn Met Ala
            260                 265                 270
Thr Ser Gly Asn Gly Gln Gly Ser Thr Thr Arg Met Asp His Glu Thr
            275                 280                 285
Ala Ser Val Leu Ser Ser Ser Thr His Ser Ala Pro Arg Arg Leu
            290                 295                 300
Thr Ser His Leu Gly Thr Lys Val Glu Met Val Tyr Ser Leu Leu Ser
305                 310                 315                 320
Met Leu Gly Thr His Asp Lys Asp Asp Met Ser Arg Thr Leu Leu Ala
            325                 330                 335
Met Ser Ser Ser Gln Asp Ser Cys Ile Ser Met Arg Gln Ser Gly Cys
            340                 345                 350
Leu Pro Leu Leu Ile Gln Leu Leu His Gly Asn Asp Lys Asp Ser Val
            355                 360                 365
Leu Leu Gly Asn Ser Arg Gly Ser Lys Glu Ala Arg Ala Arg Ala Ser
            370                 375                 380
Ala Ala Leu His Asn Ile Ile His Ser Gln Pro Asp Asp Lys Arg Gly
385                 390                 395                 400
Arg Arg Glu Ile Arg Val Leu His Leu Leu Glu Gln Ile Arg Ala Tyr
            405                 410                 415
Cys Ser Thr Cys Trp Glu Trp Gln Glu Ala His Glu Pro Gly Met Asp
            420                 425                 430
Gln Asp Lys Asn Pro Met Pro Ala Pro Val Glu His Gln Ile Cys Pro
            435                 440                 445
Ala Val Cys Val Leu Met Lys Leu Ser Phe Asp Glu Glu His Arg His
            450                 455                 460
Ala Met Asn Glu Leu Gly Gly Leu Gln Ala Ile Ala Glu Leu Leu Gln
465                 470                 475                 480
Val Asp Cys Glu Met Tyr Gly Leu Thr Asn Asp His Tyr Ser Ile Thr
            485                 490                 495
Leu Arg Arg Tyr Ala Gly Met Ala Leu Thr Asn Leu Thr Phe Gly Asp
            500                 505                 510
Val Ala Asn Lys Ala Thr Leu Cys Ser Met Lys Gly Cys Met Arg Ala
            515                 520                 525
Leu Val Ala Gln Leu Lys Ser Glu Ser Glu Asp Leu Gln Gln Val Ile
            530                 535                 540
Ala Ser Val Leu Arg Asn Leu Ser Trp Arg Ala Asp Val Asn Ser Lys
545                 550                 555                 560
Lys Thr Leu Arg Glu Val Gly Ser Val Lys Ala Leu Met Glu Cys Ala
            565                 570                 575
```

```
Leu Glu Val Lys Lys Glu Ser Thr Leu Lys Ser Val Leu Ser Ala Leu
            580                 585                 590

Trp Asn Leu Ser Ala His Cys Thr Glu Asn Lys Ala Asp Ile Cys Ala
        595                 600                 605

Val Asp Gly Ala Leu Ala Phe Leu Val Gly Thr Leu Thr Tyr Arg Ser
        610                 615                 620

Gln Thr Asn Thr Leu Ala Ile Ile Glu Ser Gly Gly Gly Ile Leu Arg
625                 630                 635                 640

Asn Val Ser Ser Leu Ile Ala Thr Asn Glu Asp His Arg Gln Ile Leu
                645                 650                 655

Arg Glu Asn Asn Cys Leu Gln Thr Leu Leu Gln His Leu Lys Ser His
            660                 665                 670

Ser Leu Thr Ile Val Ser Asn Ala Cys Gly Thr Leu Trp Asn Leu Ser
            675                 680                 685

Ala Arg Asn Pro Lys Asp Gln Glu Ala Leu Trp Asp Met Gly Ala Val
        690                 695                 700

Ser Met Leu Lys Asn Leu Ile His Ser Lys His Lys Met Ile Ala Met
705                 710                 715                 720

Gly Ser Ala Ala Ala Leu Arg Asn Leu Met Ala Asn Arg Pro Ala Lys
                725                 730                 735

Tyr Lys Asp Ala Asn Ile Met Ser Pro Gly Ser Ser Leu Pro Ser Leu
            740                 745                 750

His Val Arg Lys Gln Lys Ala Leu Glu Ala Glu Leu Asp Ala Gln His
            755                 760                 765

Leu Ser Glu Thr Phe Asp Asn Ile Asp Asn Ile Ser Pro Lys Ala Ser
        770                 775                 780

His Arg Ser Lys Gln Arg His Lys Gln Ser Leu Tyr Gly Asp Tyr Val
785                 790                 795                 800

Phe Asp Thr Asn Arg His Asp Asp Asn Arg Ser Asp Asn Phe Asn Thr
                805                 810                 815

Gly Asn Met Thr Val Leu Ser Pro Tyr Leu Asn Thr Thr Val Leu Pro
            820                 825                 830

Ser Ser Ser Ser Ser Arg Gly Ser Leu Asp Ser Ser Arg Ser Glu Lys
            835                 840                 845

Asp Arg Ser Leu Glu Arg Glu Arg Gly Ile Gly Leu Gly Asn Tyr His
        850                 855                 860

Pro Ala Thr Glu Asn Pro Gly Thr Ser Ser Lys Arg Gly Leu Gln Ile
865                 870                 875                 880

Ser Thr Thr Ala Ala Gln Ile Ala Lys Val Met Glu Glu Val Ser Ala
                885                 890                 895

Ile His Thr Ser Gln Glu Asp Arg Ser Ser Gly Ser Thr Thr Glu Leu
            900                 905                 910

His Cys Val Thr Asp Glu Arg Asn Ala Leu Arg Arg Ser Ser Ala Ala
            915                 920                 925

His Thr His Ser Asn Thr Tyr Asn Phe Thr Lys Ser Glu Asn Ser Asn
        930                 935                 940

Arg Thr Cys Ser Met Pro Tyr Ala Lys Leu Glu Tyr Lys Arg Ser Ser
945                 950                 955                 960

Asn Asp Ser Leu Asn Ser Val Ser Ser Asp Gly Tyr Gly Lys Arg
                965                 970                 975

Gly Gln Met Lys Pro Ser Ile Glu Ser Tyr Ser Glu Asp Asp Glu Ser
            980                 985                 990

Lys Phe Cys Ser Tyr Gly Gln Tyr Pro Ala Asp Leu Ala His Lys Ile
```

-continued

```
              995                1000               1005
His Ser Ala Asn His Met Asp Asp Asn Asp Gly Glu Leu Asp Thr Pro
    1010               1015               1020

Ile Asn Tyr Ser Leu Lys Tyr Ser Asp Glu Gln Leu Asn Ser Gly Arg
1025               1030               1035               1040

Gln Ser Pro Ser Gln Asn Glu Arg Trp Ala Arg Pro Lys His Ile Ile
            1045               1050               1055

Glu Asp Glu Ile Lys Gln Ser Glu Gln Arg Gln Ser Arg Asn Gln Ser
        1060               1065               1070

Thr Thr Tyr Pro Val Tyr Thr Glu Ser Thr Asp Asp Lys His Leu Lys
    1075               1080               1085

Phe Gln Pro His Phe Gly Gln Gln Glu Cys Val Ser Pro Tyr Arg Ser
1090               1095               1100

Arg Gly Ala Asn Gly Ser Glu Thr Asn Arg Val Gly Ser Asn His Gly
1105               1110               1115               1120

Ile Asn Gln Asn Val Ser Gln Ser Leu Cys Gln Glu Asp Asp Tyr Glu
            1125               1130               1135

Asp Asp Lys Pro Thr Asn Tyr Ser Glu Arg Tyr Ser Glu Glu Glu Gln
        1140               1145               1150

His Glu Glu Glu Arg Pro Thr Asn Tyr Ser Ile Lys Tyr Asn Glu
    1155               1160               1165

Glu Lys Arg His Val Asp Gln Pro Ile Asp Tyr Ser Ile Leu Lys Ala
    1170               1175               1180

Thr Asp Ile Pro Ser Ser Gln Lys Gln Ser Phe Ser Phe Lys Ser
1185               1190               1195               1200

Ser Ser Gly Gln Ser Ser Lys Thr Glu His Met Ser Ser Ser Glu
            1205               1210               1215

Asn Thr Ser Thr Pro Ser Ser Asn Ala Lys Arg Gln Asn Gln Leu His
        1220               1225               1230

Pro Ser Ser Ala Gln Ser Arg Ser Gly Gln Pro Gln Lys Ala Ala Thr
    1235               1240               1245

Cys Lys Val Ser Ser Ile Asn Gln Glu Thr Ile Gln Thr Tyr Cys Val
    1250               1255               1260

Glu Asp Thr Pro Ile Cys Phe Ser Arg Cys Ser Ser Leu Ser Ser Leu
1265               1270               1275               1280

Ser Ser Ala Glu Asp Glu Ile Gly Cys Asn Gln Thr Thr Gln Glu Ala
            1285               1290               1295

Asp Ser Ala Asn Thr Leu Gln Ile Ala Glu Ile Lys Glu Lys Ile Gly
        1300               1305               1310

Thr Arg Ser Ala Glu Asp Pro Val Ser Glu Val Pro Ala Val Ser Gln
    1315               1320               1325

His Pro Arg Thr Lys Ser Ser Arg Leu Gln Gly Ser Ser Leu Ser Ser
    1330               1335               1340

Glu Ser Ala Arg His Lys Ala Val Glu Phe Ser Ser Gly Ala Lys Ser
1345               1350               1355               1360

Pro Ser Lys Ser Gly Ala Gln Thr Pro Lys Ser Pro Glu His Tyr
            1365               1370               1375

Val Gln Glu Thr Pro Leu Met Phe Ser Arg Cys Thr Ser Val Ser Ser
        1380               1385               1390

Leu Asp Ser Phe Glu Ser Arg Ser Ile Ala Ser Ser Val Gln Ser Glu
    1395               1400               1405

Pro Cys Ser Gly Met Val Ser Gly Ile Ile Ser Pro Ser Asp Leu Pro
    1410               1415               1420
```

```
Asp Ser Pro Gly Gln Thr Met Pro Pro Ser Arg Ser Lys Thr Pro Pro
1425                1430                1435                1440

Pro Pro Pro Gln Thr Ala Gln Thr Lys Arg Glu Val Pro Lys Asn Lys
            1445                1450                1455

Ala Pro Thr Ala Glu Lys Arg Glu Ser Gly Pro Lys Gln Ala Ala Val
        1460                1465                1470

Asn Ala Ala Val Gln Arg Val Gln Val Leu Pro Asp Ala Asp Thr Leu
    1475                1480                1485

Leu His Phe Ala Thr Glu Ser Thr Pro Asp Gly Phe Ser Cys Ser Ser
1490                1495                1500

Ser Leu Ser Ala Leu Ser Leu Asp Glu Pro Phe Ile Gln Lys Asp Val
1505                1510                1515                1520

Glu Leu Arg Ile Met Pro Pro Val Gln Glu Asn Asp Asn Gly Asn Glu
            1525                1530                1535

Thr Glu Ser Glu Gln Pro Lys Glu Ser Asn Glu Asn Gln Glu Lys Glu
            1540                1545                1550

Ala Glu Lys Thr Ile Asp Ser Gly Lys Asp Leu Leu Asp Asp Ser Asp
    1555                1560                1565

Asp Asp Asp Ile Glu Ile Leu Glu Glu Cys Ile Ile Ser Ala Met Pro
    1570                1575                1580

Thr Lys Ser Ser Arg Lys Ala Lys Lys Pro Ala Gln Thr Ala Ser Lys
1585                1590                1595                1600

Leu Pro Pro Pro Val Ala Arg Lys Pro Ser Gln Leu Pro Val Tyr Lys
            1605                1610                1615

Leu Leu Pro Ser Gln Asn Arg Leu Gln Pro Gln Lys His Val Ser Phe
            1620                1625                1630

Thr Pro Gly Asp Asp Met Pro Arg Val Tyr Cys Val Glu Gly Thr Pro
            1635                1640                1645

Ile Asn Phe Ser Thr Ala Thr Ser Leu Ser Asp Leu Thr Ile Glu Ser
    1650                1655                1660

Pro Pro Asn Glu Leu Ala Ala Gly Glu Gly Val Arg Gly Gly Ala Gln
1665                1670                1675                1680

Ser Gly Glu Phe Glu Lys Arg Asp Thr Ile Pro Thr Glu Gly Arg Ser
            1685                1690                1695

Thr Asp Glu Ala Gln Gly Gly Lys Thr Ser Ser Val Thr Ile Pro Glu
        1700                1705                1710

Leu Asp Asp Asn Lys Ala Glu Glu Gly Asp Ile Leu Ala Glu Cys Ile
    1715                1720                1725

Asn Ser Ala Met Pro Lys Gly Lys Ser His Lys Pro Phe Arg Val Lys
    1730                1735                1740

Lys Ile Met Asp Gln Val Gln Gln Ala Ser Ala Ser Ser Ser Ala Pro
1745                1750                1755                1760

Asn Lys Asn Gln Leu Asp Gly Lys Lys Lys Lys Pro Thr Ser Pro Val
            1765                1770                1775

Lys Pro Ile Pro Gln Asn Thr Glu Tyr Arg Thr Arg Val Arg Lys Asn
        1780                1785                1790

Ala Asp Ser Lys Asn Asn Leu Asn Ala Glu Arg Val Phe Ser Asp Asn
        1795                1800                1805

Lys Asp Ser Lys Lys Gln Asn Leu Lys Asn Asn Ser Lys Asp Phe Asn
    1810                1815                1820

Asp Lys Leu Pro Asn Asn Glu Asp Arg Val Arg Gly Ser Phe Ala Phe
1825                1830                1835                1840
```

Asp Ser Pro His His Tyr Thr Pro Ile Glu Gly Thr Pro Tyr Cys Phe
         1845                1850                1855

Ser Arg Asn Asp Ser Leu Ser Ser Leu Asp Phe Asp Asp Asp Val
         1860                1865                1870

Asp Leu Ser Arg Glu Lys Ala Glu Leu Arg Lys Ala Lys Glu Asn Lys
         1875                1880                1885

Glu Ser Glu Ala Lys Val Thr Ser His Thr Glu Leu Thr Ser Asn Gln
         1890                1895                1900

Gln Ser Ala Asn Lys Thr Gln Ala Ile Ala Lys Gln Pro Ile Asn Arg
1905               1910                1915                1920

Gly Gln Pro Lys Pro Ile Leu Gln Lys Gln Ser Thr Phe Pro Gln Ser
         1925                1930                1935

Ser Lys Asp Ile Pro Asp Arg Gly Ala Ala Thr Asp Glu Lys Leu Gln
         1940                1945                1950

Asn Phe Ala Ile Glu Asn Thr Pro Val Cys Phe Ser His Asn Ser Ser
         1955                1960                1965

Leu Ser Ser Leu Ser Asp Ile Asp Gln Glu Asn Asn Asn Lys Glu Asn
         1970                1975                1980

Glu Pro Ile Lys Glu Thr Glu Pro Pro Asp Ser Gln Gly Glu Pro Ser
1985               1990                1995                2000

Lys Pro Gln Ala Ser Gly Tyr Ala Pro Lys Ser Phe His Val Glu Asp
         2005                2010                2015

Thr Pro Val Cys Phe Ser Arg Asn Ser Ser Leu Ser Ser Leu Ser Ile
         2020                2025                2030

Asp Ser Glu Asp Asp Leu Leu Gln Glu Cys Ile Ser Ser Ala Met Pro
         2035                2040                2045

Lys Lys Lys Lys Pro Ser Arg Leu Lys Gly Asp Asn Glu Lys His Ser
         2050                2055                2060

Pro Arg Asn Met Gly Gly Ile Leu Gly Glu Asp Leu Thr Leu Asp Leu
2065               2070                2075                2080

Lys Asp Ile Gln Arg Pro Asp Ser Glu His Gly Leu Ser Pro Asp Ser
         2085                2090                2095

Glu Asn Phe Asp Trp Lys Ala Ile Gln Glu Gly Ala Asn Ser Ile Val
         2100                2105                2110

Ser Ser Leu His Gln Ala Ala Ala Ala Ala Cys Leu Ser Arg Gln Ala
         2115                2120                2125

Ser Ser Asp Ser Asp Ser Ile Leu Ser Leu Lys Ser Gly Ile Ser Leu
         2130                2135                2140

Gly Ser Pro Phe His Leu Thr Pro Asp Gln Glu Glu Lys Pro Phe Thr
2145               2150                2155                2160

Ser Asn Lys Gly Pro Arg Ile Leu Lys Pro Gly Glu Lys Ser Thr Leu
         2165                2170                2175

Glu Thr Lys Lys Ile Glu Ser Glu Ser Lys Gly Ile Lys Gly Gly Lys
         2180                2185                2190

Lys Val Tyr Lys Ser Leu Ile Thr Gly Lys Val Arg Ser Asn Ser Glu
         2195                2200                2205

Ile Ser Gly Gln Met Lys Gln Pro Leu Gln Ala Asn Met Pro Ser Ile
         2210                2215                2220

Ser Arg Gly Arg Thr Met Ile His Ile Pro Gly Val Arg Asn Ser Ser
2225               2230                2235                2240

Ser Ser Thr Ser Pro Val Ser Lys Lys Gly Pro Pro Leu Lys Thr Pro
         2245                2250                2255

Ala Ser Lys Ser Pro Ser Glu Gly Gln Thr Ala Thr Thr Ser Pro Arg

-continued

```
            2260                2265                2270
Gly Ala Lys Pro Ser Val Lys Ser Glu Leu Ser Pro Val Ala Arg Gln
        2275                2280                2285
Thr Ser Gln Ile Gly Gly Ser Ser Lys Ala Pro Ser Arg Ser Gly Ser
    2290                2295                2300
Arg Asp Ser Thr Pro Ser Arg Pro Ala Gln Gln Pro Leu Ser Arg Pro
2305                2310                2315                2320
Ile Gln Ser Pro Gly Arg Asn Ser Ile Ser Pro Gly Arg Asn Gly Ile
            2325                2330                2335
Ser Pro Pro Asn Lys Ile Ser Gln Leu Pro Arg Thr Ser Ser Pro Ser
        2340                2345                2350
Thr Ala Ser Thr Lys Ser Ser Gly Ser Gly Lys Met Ser Tyr Thr Ser
    2355                2360                2365
Pro Gly Arg Gln Met Ser Gln Gln Asn Leu Thr Lys Gln Thr Gly Leu
        2370                2375                2380
Ser Lys Asn Ala Ser Ser Ile Pro Arg Ser Glu Ser Ala Ser Lys Gly
2385                2390                2395                2400
Leu Asn Gln Met Asn Asn Gly Asn Gly Ala Asn Lys Lys Val Glu Leu
            2405                2410                2415
Ser Arg Met Ser Ser Thr Lys Ser Ser Gly Ser Glu Ser Asp Arg Ser
        2420                2425                2430
Glu Arg Pro Val Leu Val Arg Gln Ser Thr Phe Ile Lys Glu Ala Pro
    2435                2440                2445
Ser Pro Thr Leu Arg Arg Lys Leu Glu Glu Ser Ala Ser Phe Glu Ser
        2450                2455                2460
Leu Ser Pro Ser Ser Arg Pro Ala Ser Pro Thr Arg Ser Gln Ala Gln
2465                2470                2475                2480
Thr Pro Val Leu Ser Pro Ser Leu Pro Asp Met Ser Leu Ser Thr His
            2485                2490                2495
Ser Ser Val Gln Ala Gly Gly Trp Arg Lys Leu Pro Pro Asn Leu Ser
        2500                2505                2510
Pro Thr Ile Glu Tyr Asn Asp Gly Arg Pro Ala Lys Arg His Asp Ile
    2515                2520                2525
Ala Arg Ser His Ser Glu Ser Pro Ser Arg Leu Pro Ile Asn Arg Ser
    2530                2535                2540
Gly Thr Trp Lys Arg Glu His Ser Lys His Ser Ser Ser Leu Pro Arg
2545                2550                2555                2560
Val Ser Thr Trp Arg Arg Thr Gly Ser Ser Ser Ser Ile Leu Ser Ala
            2565                2570                2575
Ser Ser Glu Ser Ser Glu Lys Ala Lys Ser Glu Asp Glu Lys His Val
        2580                2585                2590
Asn Ser Ile Ser Gly Thr Lys Gln Ser Lys Glu Asn Gln Val Ser Ala
        2595                2600                2605
Lys Gly Thr Trp Arg Lys Ile Lys Glu Asn Glu Phe Ser Pro Thr Asn
    2610                2615                2620
Ser Thr Ser Gln Thr Val Ser Ser Gly Ala Thr Asn Gly Ala Glu Ser
2625                2630                2635                2640
Lys Thr Leu Ile Tyr Gln Met Ala Pro Ala Val Ser Lys Thr Glu Asp
            2645                2650                2655
Val Trp Val Arg Ile Glu Asp Cys Pro Ile Asn Asn Pro Arg Ser Gly
        2660                2665                2670
Arg Ser Pro Thr Gly Asn Thr Pro Pro Val Ile Asp Ser Val Ser Glu
    2675                2680                2685
```

-continued

Lys Ala Asn Pro Asn Ile Lys Asp Ser Lys Asp Asn Gln Ala Lys Gln
            2690                2695                2700

Asn Val Gly Asn Gly Ser Val Pro Met Arg Thr Val Gly Leu Glu Asn
2705                2710                2715                2720

Arg Leu Asn Ser Phe Ile Gln Val Asp Ala Pro Asp Gln Lys Gly Thr
            2725                2730                2735

Glu Ile Lys Pro Gly Gln Asn Asn Pro Val Pro Val Ser Glu Thr Asn
        2740                2745                2750

Glu Ser Ser Ile Val Glu Arg Thr Pro Phe Ser Ser Ser Ser Ser Ser
        2755                2760                2765

Lys His Ser Ser Pro Ser Gly Thr Val Ala Ala Arg Val Thr Pro Phe
    2770                2775                2780

Asn Tyr Asn Pro Ser Pro Arg Lys Ser Ser Ala Asp Ser Thr Ser Ala
2785                2790                2795                2800

Arg Pro Ser Gln Ile Pro Thr Pro Val Asn Asn Asn Thr Lys Lys Arg
            2805                2810                2815

Asp Ser Lys Thr Asp Ser Thr Glu Ser Ser Gly Thr Gln Ser Pro Lys
        2820                2825                2830

Arg His Ser Gly Ser Tyr Leu Val Thr Ser Val
    2835                2840

<210> SEQ ID NO 31
<211> LENGTH: 65
<212> TYPE: DNA
<213> ORGANISM: Artificial Sequence
<220> FEATURE:
<223> OTHER INFORMATION: Description of Artificial
      Sequence:source:synthesized
<220> FEATURE:
<221> NAME/KEY: misc_feature
<222> LOCATION: (9)..(17)
<223> OTHER INFORMATION: N=A, T, C or G
<220> FEATURE:
<221> NAME/KEY: misc_feature
<222> LOCATION: (24)..(32)
<223> OTHER INFORMATION: N=A, T, C, or G
<220> FEATURE:
<221> NAME/KEY: misc_feature
<222> LOCATION: (39)..(41)
<223> OTHER INFORMATION: N=A, T, C  or G
<220> FEATURE:
<221> NAME/KEY: misc_feature
<222> LOCATION: (51)..(53)
<223> OTHER INFORMATION: N=A, T, C or G

<400> SEQUENCE: 31
cggaattcnn nnnnnnnaac agcnnnnnnn nnaatgaann ncaaagtctg nnntgaggat     60
cctca                                                                65

<210> SEQ ID NO 32
<211> LENGTH: 65
<212> TYPE: DNA
<213> ORGANISM: Artificial Sequence
<220> FEATURE:
<223> OTHER INFORMATION: Description of Artificial
      Sequence:source:synthesized
<220> FEATURE:
<221> NAME/KEY: misc_feature
<222> LOCATION: (18)..(23)
<223> OTHER INFORMATION: N= A, T ,C or G
<220> FEATURE:
<221> NAME/KEY: misc_feature
<222> LOCATION: (33)..(38)
<223> OTHER INFORMATION: N=A, T, C or G
<220> FEATURE:

```
<221> NAME/KEY: misc_feature
<222> LOCATION: (42)..(50)
<223> OTHER INFORMATION: N=A, T, C or G

<400> SEQUENCE: 32
cggaattcga ctcagaannn nnnaacttca gannnnnnat cnnnnnnnnn gtctgaggat    60
cctca                                                               65

<210> SEQ ID NO 33
<211> LENGTH: 65
<212> TYPE: DNA
<213> ORGANISM: Artificial Sequence
<220> FEATURE:
<223> OTHER INFORMATION: Description of Artificial
      Sequence:source:synthesized
<220> FEATURE:
<221> NAME/KEY: misc_feature
<222> LOCATION: (9)..(53)
<223> OTHER INFORMATION: N=A, T, C or G

<400> SEQUENCE: 33
cggaattcnn nnnnnnnnnn nnnnnnnnnn nnnnnnnnnn nnnnnnnnnn nnntgaggat    60
cctca                                                               65

<210> SEQ ID NO 34
<211> LENGTH: 4
<212> TYPE: PRT
<213> ORGANISM: Artificial Sequence
<220> FEATURE:
<223> OTHER INFORMATION: Description of Artificial
      Sequence:source:motif

<400> SEQUENCE: 34

Gly Leu Gly Phe
  1
```

METHOD OF PREPARING A PROTEIN ARRAY BASED ON BIOCHEMICAL PROTEIN-PROTEIN INTERACTION

The subject matter disclosed herein was made with Government support under Grant No. R01GM55147-01 from the National Institutes of Health of the United States Department of Health and Human Services. Accordingly, the U.S. Government may have certain rights in this application.

BACKGROUND

Throughout this application, various publications are referenced by author and date. Full citations for these publications may be found listed alphabetically at the end of the specification immediately preceding Sequence Listing and the claims. The disclosures of these publications in their entireties are hereby incorporated by reference into this application in order to more fully describe the state of the art as known to those skilled therein as of the date of the invention described and claimed herein.

Fas (APO-1/CD95) and its ligand have been identified as important signal-mediators of apoptosis (Itoh, et al. 1991) The structural organization of Fas (APO-1/CD95) has suggested that it is a member of the tumor necrosis factor receptor superfamily, which also includes the p75 nerve growth factor receptor (NGFR) (Johnson, et al. 1986), the T-cell-activation marker CD27 (Camerini, et al. 1991), the Hodgkin-lymphoma-associated antigen CD30 (Smith, et al. (1993), the human B cell antigen CD40 (Stamenkovic, et al. 1989), and T cell antigen OX40 (Mallett, et al. 1990). Genetic mutations of both Fas and its ligand have been associated with lymphoproliferative and autoimmune disorders in mice (Watanabe-Fukunaga, et al. 1992; Takahashi, et al. 1994). Furthermore, alterations of Fas expression level have been thought to lead to the induction of apoptosis in T-cells infected with human immunodeficiency virus (HIV) (Westendorp, et al. 1995).

Several Fas-interacting signal transducing molecules, such as Fas-associated phosphatase-1 (FAP-1)(FIG. 1) (Sato, et al. 1995), FADD/MORT1 (Chinnaiyan, et al. 1995; Boldin, et al. 1995; Kischkel, et al. 1995) and RIP (Stanger, et al. 1995), have been identified using yeast two-hybrid and biochemical approaches. All but FAP-1 associate with the functional cell death domain of Fas and overexpression of FADD/MORT1 or RIP induces apoptosis in cells transfected with these proteins. In contrast, FAP-1 is the only protein that associates with the negative regulatory domain (C-terminal 15 amino acids) (Ito, et al. 1993) of Fas and that inhibits Fas-induced apoptosis. FAP-1 (PTPN13) has several alternatively-spliced forms that are identical to PTP-BAS/hPTP1E/PTPL1, (Maekawa, et al. 1994; Banville, et al. 1994; Saras, et al. 1994) and contains a membrane-binding region similar to those found in the cytoskeleton-associated proteins, ezrin, (Gould et al. 1989) radixin (Funayama et al. 1991) moesin (Lankes, et al. 1991), neurofibromatosis type II gene product (NFII) (Rouleau, et al. 1993), and protein 4.1 (Conboy, et al. 1991), as well as in the PTPases PTPH1 (Yang, et al. 1991), PTP-MEG (Gu, et al. 1991), and PTPD1 (Vogel, et al. 1993). FAP-1 intriguingly contains six GLGF (PDZ/DHR) (SEQ ID NO:34) repeats that are thought to mediate intra-and inter-molecular interactions among protein domains. The third GLGF (SEQ ID NO:34) repeat of FAP-1 was first identified as a domain showing the specific interaction with the C-terminus of Fas receptor (Sato, et al. 1995). This suggests that the GLGF (SEQ ID NO:34) domain may play an important role in targeting proteins to the submembranous cytoskeleton and/or in regulating biochemical activity. GLGF (SEQ ID NO:34) repeats have been previously found in guanylate kinases, as well as in the rat post-synaptic density protein (PSD-95) (Cho, et al. 1992), which is a homolog of the Drosophila tumor suppressor protein, lethal-(1)-disc-large-1 [dlg-1] (Woods, et al 1991; Kitamura, et al. 1994). These repeats may mediate homo- and hetero-dimerization, which could potentially influence PTPase activity, binding to Fas, and/or interactions of FAP-1 with other signal transduction proteins. Recently, it has also been reported that the different PDZ domains of proteins interact with the C-terminus of ion channels and other proteins (FIG. 1) (TABLE 1) (Kornau, et al. 1995; Kim, et al. 1995; Matsumine, et al. 1996).

TABLE 1

Proteins that interact with PDZ domains.

| Protein | C-terminal sequence | Associated protein | Reference |
|---|---|---|---|
| Fas (APO-1/CD95) | SLV | FAP-1 | 2 |
| NMDA receptor NR2 subunit | SDV | PSD95 | 3 |
| Shaker-type K+ channel | TDV | PSD95 & DLG | 4 |
| APC | TEV | DLG | 5 |

A recent trend in biology, biotechnology and medicine is the use of arrays of immobilized biological compounds in studies of immunoassays and enzymatic reactions (see Mendoza, et al. 1999; Arenkov, et al. 2000). For example, mass-sensing, multianalyte microarray immunoassays have been performed (Rowe, et al. 1998; Silzel, et al. 1998). The use of arrays allows for large scale and high-throughput studies of multiple samples in parallel. Integration of microarray technology into the experimental methodology also may increase efficiency in many instances, such as through reducing the volume of samples and reagents required.

It would be desirable to have high-throughput and low cost methodologies for preparing protein arrays based on protein-protein interaction, and which keep the proteins in a functionally active state and allow, for example, multiple drug screenings under physiological conditions.

SUMMARY OF THE INVENTION

This disclosure provides a method of preparing a protein array based on biochemical protein-protein interaction, comprising (a) depositing on a substrate an array of a first protein, the first protein comprising a PDZ domain, and (b) applying a second protein, which comprises an amino acid sequence (S/T)—X—(V/I/L)—COOH, to the first protein array, the amino acid sequence (S/T)—X—(V/I/L)—COOH of the second protein binding to the PDZ domain of the first protein, wherein each hyphen represents a peptide bond, each parenthesis encloses amino acids which are alternatives to one other, each slash within such parentheses separates the alternative amino acids, and the X represents any amino acid which is selected from the group comprising the twenty naturally occurring amino acids.

This disclosure also provides a method of preparing a protein array, (a) depositing on a substrate an array of first proteins, each first protein comprising a corresponding PDZ domain, and (b) applying a second protein, which comprises an amino acid sequence (S/T)—X—(V/I/L)—COOH, to the array of first proteins, the amino acid sequence (S/T)—X—(V/I/L)—COOH of the second protein, for each of the first proteins, binding to the PDZ domain of the first protein, wherein each hyphen represents a peptide bond, each parenthesis encloses amino acids which are alternatives to one other, each slash within such parentheses separates the alternative amino acids, and the X represents any amino acid which is selected from the group comprising the twenty naturally occurring amino acids.

This disclosure also provides a method of preparing a protein array, (a) depositing on a substrate an array of a first protein, the first protein comprising a PDZ domain, and (b) applying a plurality of second proteins, each of which comprises a corresponding amino acid sequence (S/T)—X—(V/I/L)—COOH, to corresponding elements of the first protein array, for each of the second proteins, the amino acid sequence (S/T)—X—(V/I/L)—COOH of the second protein binding to the PDZ domain of the first protein in the corresponding array element, wherein each hyphen represents a peptide bond, each parenthesis encloses amino acids which are alternatives to one other, each slash within such parentheses separates the alternative amino acids, and the X represents any amino acid which is selected from the group comprising the twenty naturally occurring amino acids.

This disclosure also provides a method of preparing a protein array, comprising (a) depositing on a substrate an array of a first polypeptide, the first polypeptide comprising a PDZ domain, and (b) applying a second polypeptide which comprises an amino acid sequence (S/T)—X—(V/I/L)—COOH to the first polypeptide array, the amino acid sequence (S/T)—X—(V/I/L)—COOH of the second polypeptide binding to the PDZ domain of the first polypeptide, wherein each hyphen represents a peptide bond, each parenthesis encloses amino acids which are alternatives to one other, each slash within such parentheses separates the alternative amino acids, and the X represents any amino acid which is selected from the group comprising the twenty naturally occurring amino acids.

BRIEF DESCRIPTION OF THE FIGURES

FIGS. 2A, 2B, 2C and 2D. Mapping of the minimal region of the C-terminal of Fas required for the binding to FAP-1. Numbers at right show each independent clone (FIGS. 2C and 2D).

2A. Strategy for screening of a random peptide library by the yeast two-hybrid system.

2B. Alignment of the C-terminal 15 amino acids of Fas between human (Sequence I.D. No. 5), rat (Sequence I.D. No. 6), and mouse (Sequence I.D. No. 7).

2C. The results of screening a semi-random peptide library. Top row indicates the amino acids which were fixed based on the homology between human and rat. Dash lines show unchanged amino acids.

2D. The results of screening a random peptide library (Sequence I.D. No. 8, Sequence I.D. No. 9, Sequence I.D. No. 10, Sequence I.D. No. 11, Sequence I.D. No. 12, Sequence I.D. No. 13, Sequence I.D. No. 14, Sequence I.D. No. 15, Sequence I.D. No. 16, Sequence I.D. No. 17, respectively).

Figure 1:
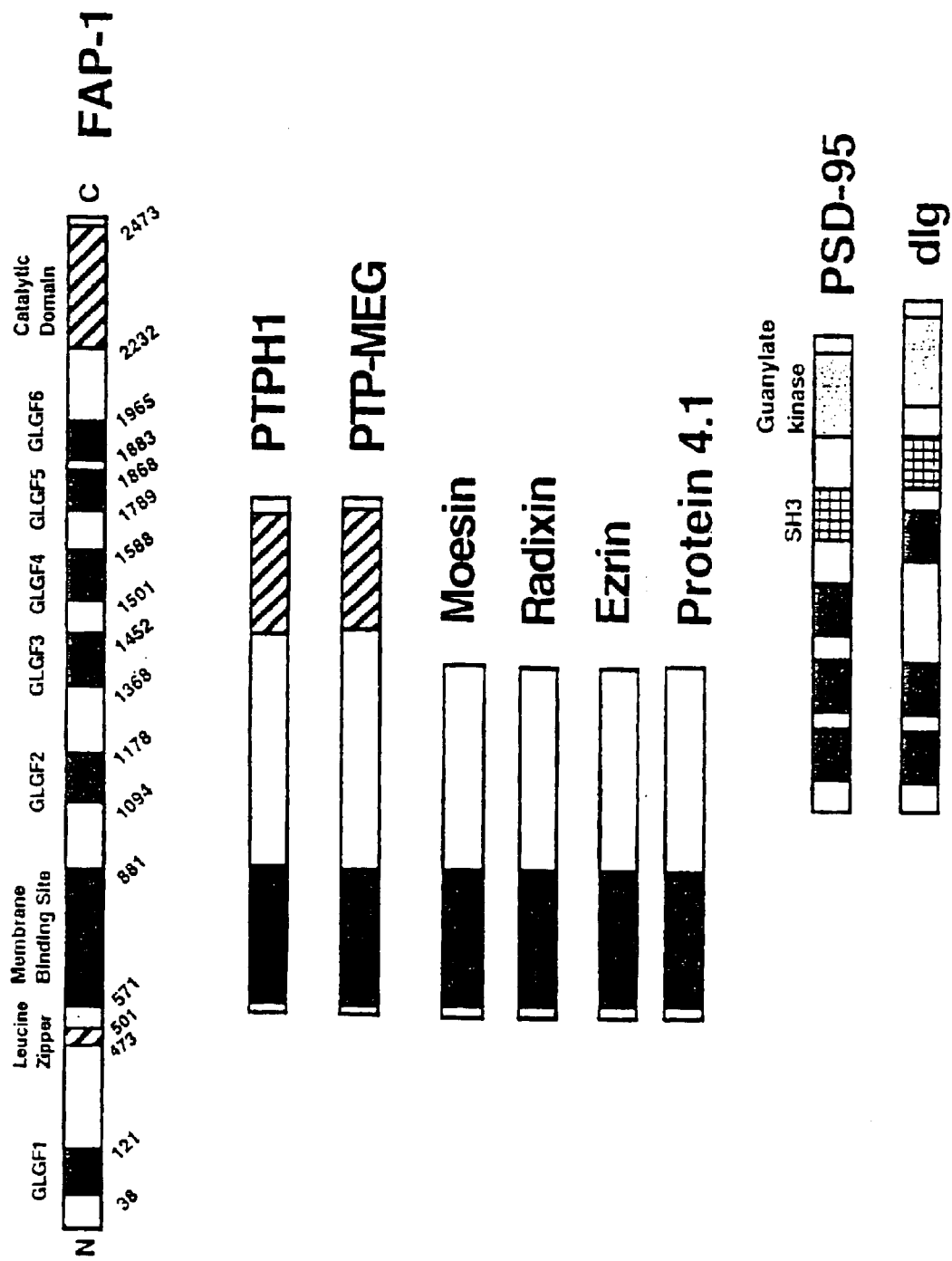
FIG. 1. Diagram of Fas-associated phosphatase-1 protein, showing the six GLGF (PDZ/DHR) domain repeats (Sequence I.D. No. 2); comparison of similar membrane binding sites with other proteins and proteins that contain GLGF (PDZ/DHR) repeats (Sequence I.D. No. 2).
Figure 3B:
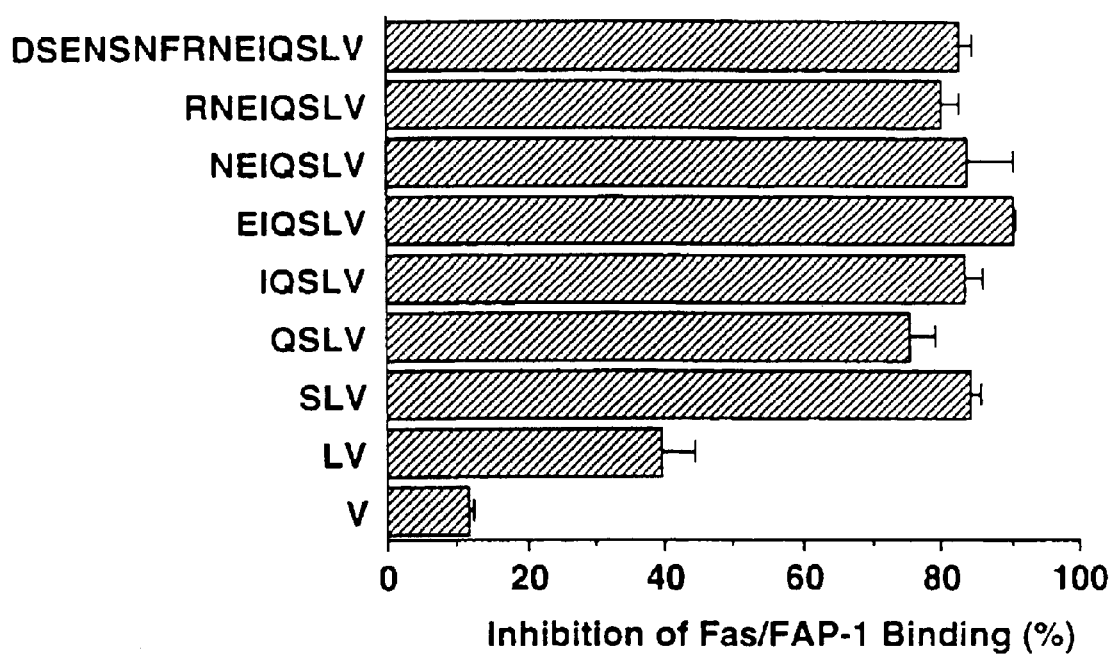
Figure 3C:
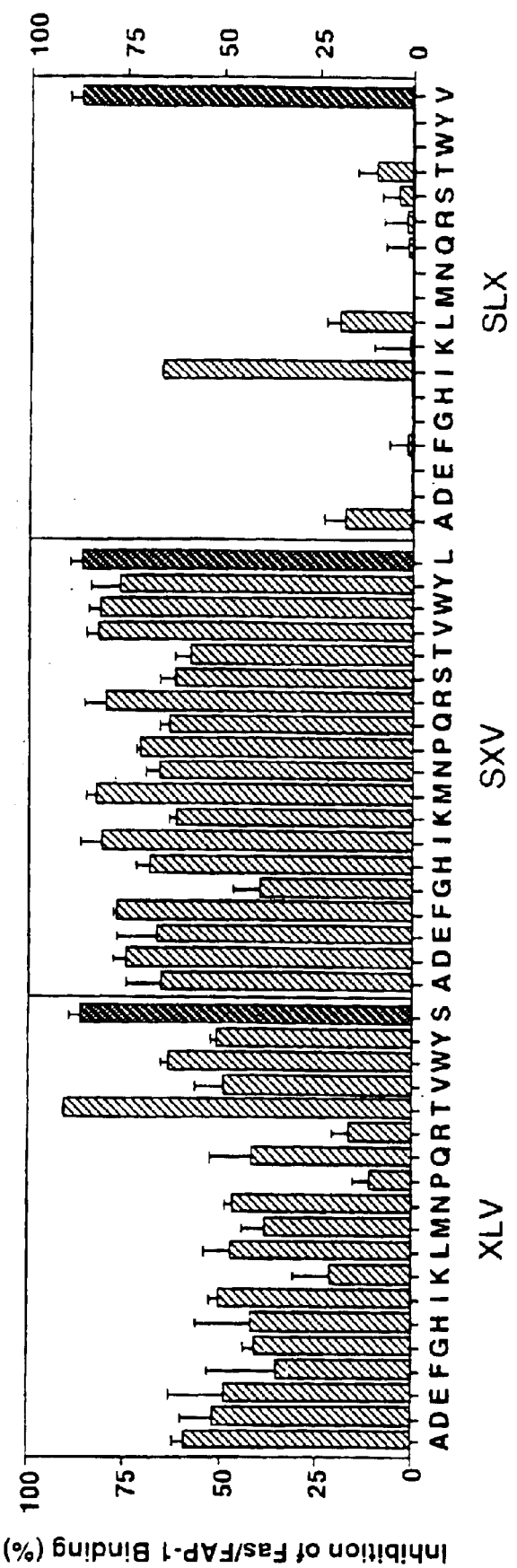

FIGS. 3A, 3B and 3C. Inhibition assay of Fas/FAP-1 binding in vitro.

3A. Inhibition assay of Fas/FAP-1 binding using the C-terminal 15 amino acids of Fas. GST-Fas fusion protein (191–355) was used for in vitro binding assay (lane 1, 3–10). GST-Fas fusion protein (191–320) (lane 2) and 1 mM human PAMP (N-terminal 20 amino acids of proadrenomedullin, M. W. 2460.9) (lane 3) were used as negative controls. The concentrations of the C-terminal 15 amino acids added were 1 (lane 4), 3 (lane 5), 10 (lane 6), 30 (lane 7), 100 (lane 8), 300 (lane 9), and 1000 µM (lane 10).

3B. Inhibition assay of Fas/FAP-1 binding using the truncated peptides corresponding to the C-terminal 15 amino acids of Fas. All synthetic peptides were acetylated for this inhibition assay (Sequence I.D. No. 4, Sequence I.D. No. 18, Sequence I.D. No. 19, Sequence I.D. No. 20, Sequence I.D. No. 21, Sequence I.D. No. 22, Sequence I.D. No. 23, respectively).

3C. Inhibitory effect of Fas/FAP-1 binding using the scanned tripeptides.

FIGS. 4A, 4B, 4C and 4D.

4A. Interaction of the C-terminal 3 amino acids of Fas with FAP-1 in yeast.

4B. Interaction of the C-terminal 3 amino acids of Fas with FAP-1 in vitro.

4C. Immuno-precipitation of native Fas with GST-FAP-1.

4D. Inhibition of Fas/FAP-1 binding with Ac-SLV or Ac-SLY.

FIGS. 5A, 5B, 5C, 5D, 5E and 5F. Microinjection of Ac-SLV into the DLD-1 cell line. Triangles identify the cells both that were could be microinjected with Ac-SLV and that showed condensed chromatin identified. On the other hand, only one cell of the area appeared apoptotic when microinjected with Ac-SLY.

5A. Representative examples of the cells microinjected with Ac-SLV in the presence of 500 ng/ml CH11 are shown in phase contrast.

5B. Representative examples of the cells microinjected with AC-SLY in the presence of 500 ng/ml CH11 are shown in phase contrast.

5C. Representative examples of the cells microinjected with Ac-SLV in the presence of 500 ng/ml CH11 are shown stained with FITC.

5D. Representative examples of the cells microinjected with AC-SLY in the presence of 500 ng/ml CH11 are shown stained with FITC.

5E. Representative examples of the cells microinjected with Ac-SLV in the presence of 500 ng/ml CH11 are shown with fluorescent DNA staining with Hoechst 33342.

5F. Representative examples of the cells microinjected with AC-SLY in the presence of 500 ng/ml CH11 are shown in fluorescent DNA staining with Hoechst 33342.

Figure 6:
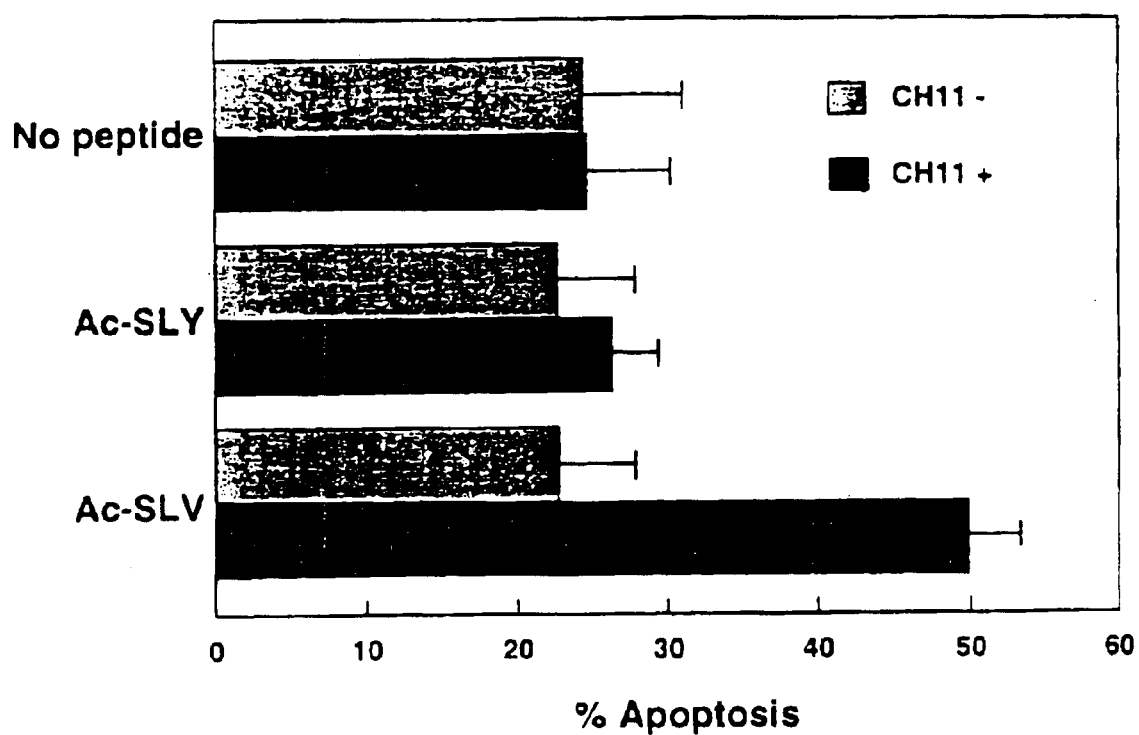

FIG. 6. Quantitation of apoptosis in microinjected DLD-1 cells.

FIGS. 7A, 7B, 7C, 7D, 7E, 7F, 7G, and 7H.

7A. Amino acid sequence of human nerve growth factor receptor (Sequence I.D. No. 24).

7B. Amino acid sequence of human CD4 receptor (Sequence I.D. No. 25).

7C. The interaction of Fas-associated phosphatase-1 to the C-terminal of nerve growth factor receptor (NGFR) (p75).

7D. Amino acid sequence of human colorectal mutant cancer protein (Sequence I.D. No. 26).

7E. Amino acid sequence of protein kinase C, alpha type (Sequence I.D. No. 27).

7F. Amino acid sequence of serotonin 2A receptor (Sequence I.D. No. 28).

7G. Amino acid sequence of serotonin 2B receptor (Sequence I.D. No. 29).

7H. Amino acid sequence of adenomatosis polyposis *coli* protein (Sequence I.D. No. 30).

Figure 8:
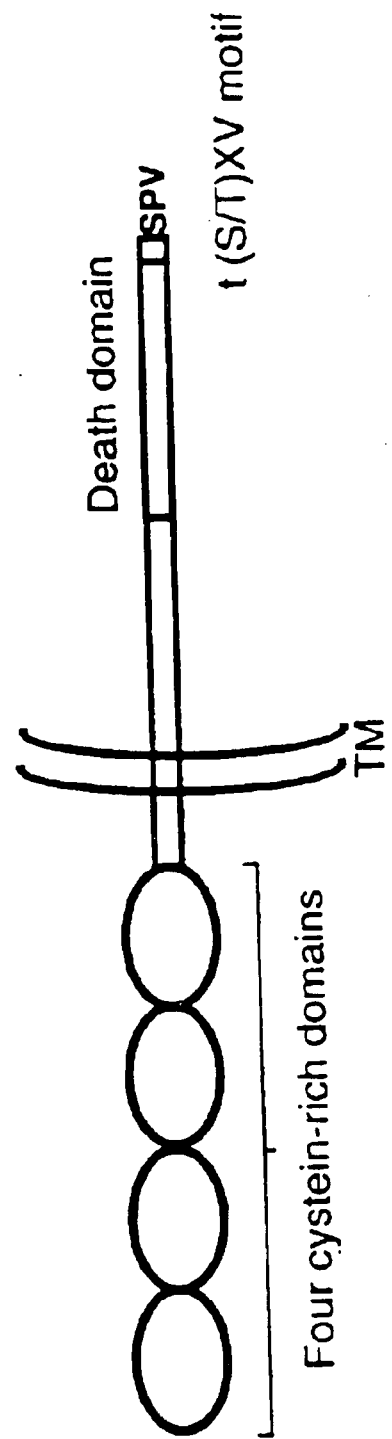

FIG. 8. Representation of the structural characteristics of p75 NGFR (low-affinity nerve growth factor receptor).

FIG. 9. Comparison of the C-terminal ends of Fas and p75 NGFR.

Figure 10:
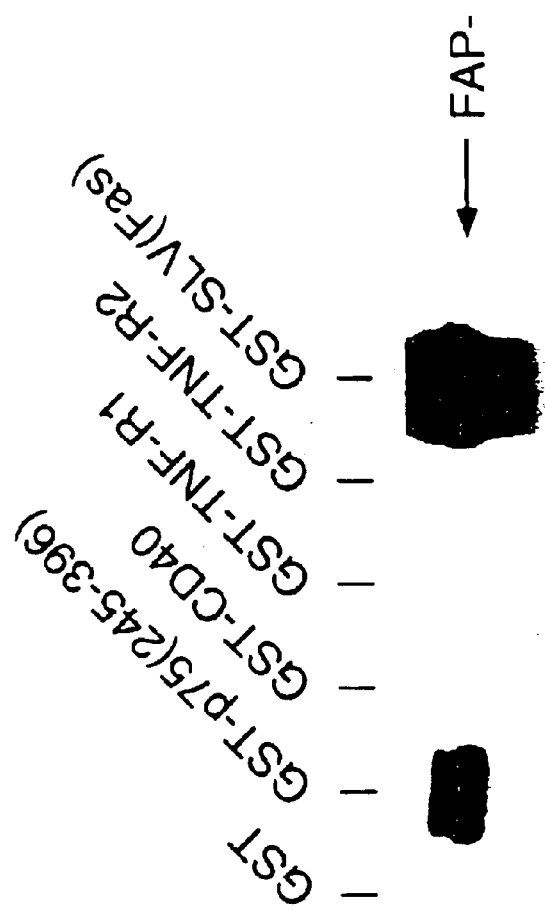

FIG. 10. In vitro interaction of $^{35}$S-labeled FAP-1 with various receptors expressed as GST fusion proteins. The indicated GST fusion proteins immobilized on glutathione-Sepharose beads were incubated with in vitro translated, $^{35}$S-labeled FAP-1 protein. After the beads were washed, retained FAP-1 protein was analyzed by SDS-PAGE and autoradiography.

Figure 11B:
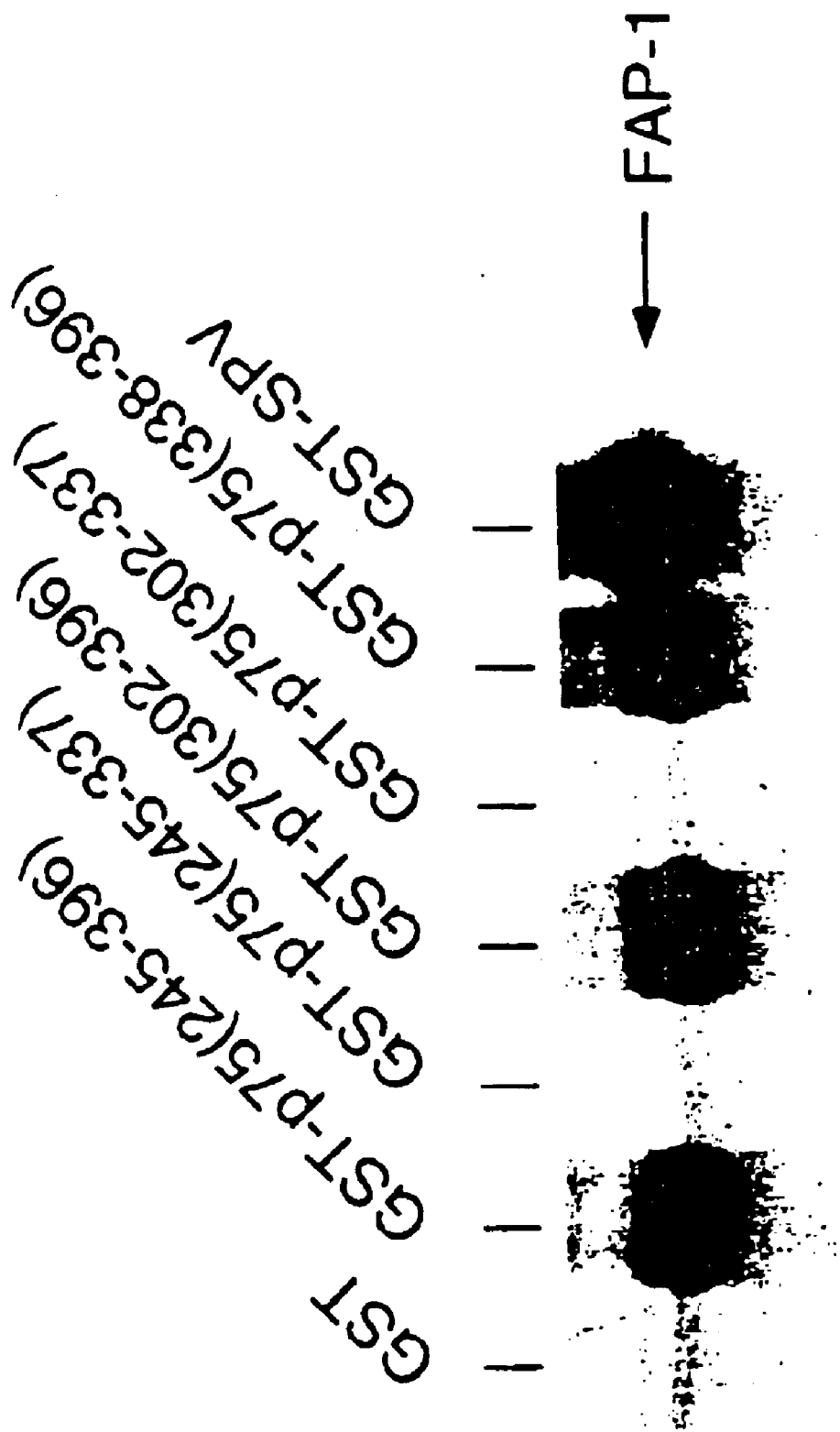

FIGS. 11A and 11B. In vitro interaction $^{35}$S-labeled FAP-1 with GST-p75 deletion mutants.

11A. Schematic representation of the GST fusion proteins containing the cytoplasmic domains of p75 and p75 deletion mutants. Binding of FAP-1 to the GST fusion proteins with various p75 deletion mutants is depicted at the right and is based on data from (2B).

11B. Interaction of in vitro translated, $^{35}$S-labeled FAP-1 protein with various GST fusion proteins immobilized on glutathione-Sepharose beads. After the beads were washed, retained FAP-1 protein was analyzed by SDS-PAGE and autoradiography.

FIG. 12. The association between LexA-C-terminal cytoplasmic region of p75NGFR and VP16-FAP-1. The indicated yeast strains were constructed by transformation and the growth of colonies was tested. +/− indicates the growth of colonies on his⁻ plate.

FIGS. 13A–13C provide schematic representations of a method of preparing a protein array based on biochemical protein-protein interaction, according to an embodiment of the present disclosure.

Figure 14A:
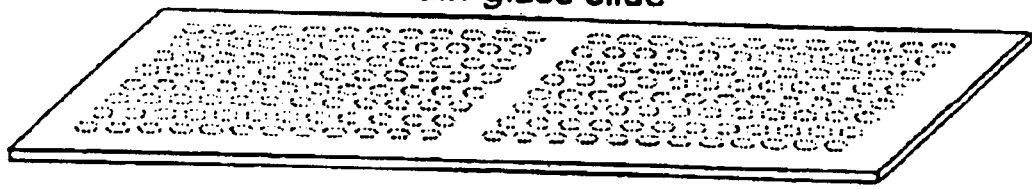
Figure 14B:
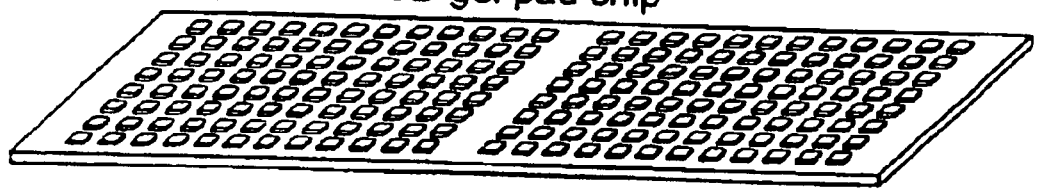
Figure 14C:
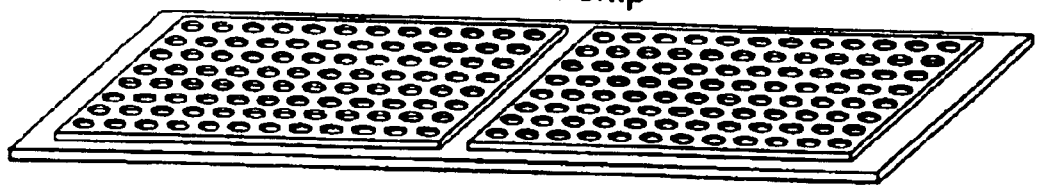

FIGS. 14A–14C provide schematic representations of some exemplary types of substrates that may be used for preparing a protein array based on biochemical protein-protein interaction.

DETAILED DESCRIPTION

As used herein, amino acid residues are abbreviated as follows: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.

In order to facilitate an understanding of the material which follows, one may refer to Sambrook, et al., 1989 for certain frequently occurring methods and/or terms which are described therein.

The present disclosure provides a method of preparing a protein array based on biochemical protein-protein interaction, comprising the steps of: (a) depositing on a substrate an array of a first protein, the first protein comprising a PDZ domain; and (b) applying a second protein, which comprises an amino acid sequence (S/T)—X—(V/I/L)—COOH, to the first protein array, the amino acid sequence (S/T)—X—(V/I/L)—COOH of the second protein binding to the PDZ domain of the first protein. Each hyphen represents a peptide bond, each parenthesis encloses amino acids which are alternatives to one other, each slash within such parentheses separates the alternative amino acids, and the X represents any amino acid which is selected from the group comprising the twenty naturally occurring amino acids.

The amino acid sequence (S/T)—X—(V/I/L) may be fused to the C-terminal of the second protein.

The protein array may be maintained under physiological condition, and used to screen one or more drug targets.

Further, the first protein deposited in step (a) may be in a soluble buffer or immobilized in a gel.

Further, the substrate may include a plurality of microwells contained therein, and the first protein is deposited in step (a) into the microwells. In another embodiment, the substrate may include a glass plate, and the first protein array is printed onto the glass plate in step (a). According to another embodiment, the substrate may include a glass plate and a plurality of gel pads on the glass plate, and the first protein is deposited in step (a) onto the gel pads. In yet another embodiment, the substrate comprises one or more filter membranes. In any event, the first protein may be deposited on the substrate by a robot.

Further, the array may include an oligonucleotide, a sugar, messenger RNA and/or DNA.

In addition, the arrays prepared with the methodologies provided by this disclosure may include, but are not limited to, antibodies, inorganic compounds, organic compounds, peptides, peptidomimetic compounds, polypeptides or proteins, fragments or derivatives which share some or all properties, e.g. fusion proteins. The components of the arrays may be naturally occurring and obtained by purification, or may be non-naturally occurring and obtained by synthesis. Proteins, enzymes, antibodies, compositions, etc., may be obtained, when available, from commercial sources, such as Sigma (U.S.A.). Exemplary methodologies for synthesizing (for example, 6y using cDNA expression libraries or chemical synthesis of polypeptide followed by refolding into native proteins) or otherwise obtaining the proteins (or, for example, other polypeptides or compositions) for preparing the arrays are provided infra. Further, one skilled in the art would know that other well-known methodologies may also (or alternatively) be used.

Further, the first protein array which is deposited on the substrate need not be a single protein, but rather may be a plurality of different proteins having one or more PDZ domains. Similarly, the second protein which is applied to the protein array need not be a single protein, but rather may be a plurality of different proteins which comprise one or more amino acid sequences (S/T)—X—(V/I/L)—COOH.

Thus, the present disclosure also provides a method of preparing a protein array, comprising the steps of: (a) depositing on a substrate an array of first proteins, each first protein comprising a corresponding PDZ domain; and (b) applying a second protein, which comprises an amino acid sequence (S/T)—X—(V/I/L)—COOH, to the array of first proteins, the amino acid sequence (S/T)—X—(V/I/L)—COOH of the second protein, for each of the first proteins, binding to the PDZ domain of the first protein. Each hyphen represents a peptide bond, each parenthesis encloses amino acids which are alternatives to one other, each slash within such parentheses separates the alternative amino acids, and the X represents any amino acid which is selected from the group comprising the twenty naturally occurring amino acids.

The present disclosure also provides a method of preparing a protein array, comprising the steps of: (a) depositing on a substrate an array of a first protein, the first protein comprising a PDZ domain; and (b) applying a plurality of second proteins, each of which comprises a corresponding amino acid sequence (S/T)—X—(V/I/L)—COOH, to corresponding elements of the first protein array, for each of the second proteins, the amino acid sequence (S/T)—X—(V/I/L)—COOH of the second protein binding to the PDZ domain of the first protein in the corresponding array element. Each hyphen represents a peptide bond, each parenthesis encloses amino acids which are alternatives to one other, each slash within such parentheses separates the alternative amino acids, and the X represents any amino acid which is selected from the group comprising the twenty naturally occurring amino acids.

The present disclosure also provides a method of preparing a protein array, comprising the steps of: (a) depositing on a substrate an array of a first polypeptide, the first polypeptide comprising a PDZ domain; and (b) applying a second polypeptide which comprises an amino acid sequence (S/T)—X—(V/I/L)—COOH to the first polypeptide array, the amino acid sequence (S/T)—X—(V/I/L)—COOH of the second polypeptide binding to the PDZ domain of the first polypeptide. Each hyphen represents a peptide bond, each parenthesis encloses amino acids which are alternatives to one other, each slash within such parentheses separates the alternative amino acids, and the X represents any amino acid which is selected from the group comprising the twenty naturally occurring amino acids. Further, the array may include an oligonucleotide, a sugar, messenger RNA and/or DNA.

The following exemplary embodiments and experimental details sections are set forth to aid in an understanding of the subject matter of this disclosure but are not intended to, and should not be construed to, limit in any way the invention as set forth in the claims which follow thereafter.

Exemplary Embodiments

Some embodiments of protein array preparation are described exemplarily below, with reference to FIGS. 13A–13C and 14A–14C, to illustrate some methodologies contemplated by the subject disclosure. One skilled in the art would recognize that these methodologies (and other aspects of the disclosure described herein) may be adapted for preparing arrays that include one or more other polypeptides, oligonucleotides, sugars, messenger RNAs, DNAs, and/or other compounds.

An array of first protein spots P is deposited on a substrate (for example, a glass slide) [FIG. 13A]. A second protein (A), which comprises an amino acid sequence (S/T)—X—(V/I/L)—COOH, is applied to the first protein array [FIG. 13B]. The amino acid sequence (S/T)—X—(V/I/L)—COOH of the second protein (A) binds to the PDZ domain of the first protein (P) [FIG. 13C]. The protein array may be used to screen drugs X, Y, Z, etc.

According to one embodiment, a substrate comprising a glass plate and a plurality of microwells (FIG. 14C) formed by, for example, an enclosing hydrophobic Teflon mask may be used (see, for example, Mendoza, et al. 1999). The protein having a PDZ domain is dissolved in a buffered solution. The protein solution is then printed as an array on the substrate through, for example, a capillary-based print head attached to a X-Y-Z robot (or another type of microdispensing liquid handling robot system). By using an automated robotic system with the open microarray, a low-cost, highly parallel assay format is feasible.

The protein may also be printed onto a treated glass slide without wells (FIG. 14A). However, use of such a substrate has the disadvantage of having higher evaporation and a greater risk of cross contamination.

According to another embodiment, gels (and gel pads) may be used to immobilize the protein having a PDZ domain. Preparation of protein microchips using gel pads is described by, for example, Arenkov, et al. 2000.

For example, according to one embodiment using gel pads, the gel pads are deposited as a micromatrix on a glass slide (FIG. 14B) and then treated according to the composition of the gel pads (for example, photopolymerization may be used for polyacrylamide gel pads). The protein, which may be dissolved in a (for example, phosphate) buffered solution, is then transferred onto the gel pads, for example, via a pin by using a robot or a manual device. Preferably, the pin and micromatrix are kept at dew point to avoid evaporation of the protein solution. Next, the protein is chemically attached to the gels. Depending on the composition of the gel, any of a number of methodologies may be used.

An advantage of using gel support for fixation of biological compounds is its large capacity for immobilized compounds. In addition, the gel pads in the array are separated from each other by a hydrophobic surface. Therefore, gel pad arrays can be used as micro-test tubes to carry out specific interactions and chemical and enzymatic procedures with microchip substances.

Filter membranes also may be used to immobilize the protein. An appropriately selected membrane passively binds to, and thereby immobilizes, the protein, to produce protein filters.

In addition, the protein solution may be labeled by covalent linkage of a fluorecent dye to the amino groups on the protein. Fluorescence microscopy methodologies may be in conjunction with the protein-protein interaction (described exemplarily below), for example, to screen drug targets.

After an array of the first protein is deposited on the substrate through, for example, one of the methodologies described above, a second protein which comprises an amino acid sequence (S/T)—X—(V/I/L)—COOH is applied to the micromatrix. The amino acid sequence (S/T)—X—(V/I/L)—COOH of the second protein binds to the PDZ domain of the first protein. The interaction between the first and second proteins is described below. After the second protein is applied, a wash may be applied.

The specific embodiments described herein are illustrative, and many variations can be introduced on these embodiments without departing from the spirit of the disclosure or from the scope of the appended claims. Elements and/or features of different illustrative embodiments may be combined with each other and/or substituted for each other within the scope of this disclosure and appended claims.

For example, in some additional embodiments, the first protein which is deposited as an array on the substrate may comprise the amino acid sequence (S/T)—X—(V/I/L)—COOH, and the second protein which is applied to the first protein array may comprise the PDZ domain.

Additional variations to the embodiments described herein may be apparent to one of ordinary skill in the art from reading U.S. patent applications Ser. Nos. 08/681,219 (filed Jul. 22, 1996) (pending as of Dec. 2, 2003) and 09/230,111 (filed May 17, 1999) (pending as of Dec. 2, 2003) . The contents of U.S. Ser. Nos. 08/681,219 and 09/230,111 are hereby incorporated by reference.

Experimental methodologies and data in connection with the subject matter of this disclosure is illustrated in the Experimental Details section which follows.

First Series of Experiments
Experimental Details
Methods and Materials
1. Screening a Semi-random and Random Peptide Library.

To create numerous mutations in a restricted DNA sequence, PCR mutagenesis with degenerate oligonucleotides was employed according to a protocol described elsewhere (Hill, et al. 1987). Based on the homology between human and rat, two palindromic sequences were designed for construction of semi-random library. The two primers used were 5'-CGGAATTCNNNNNNNNNAACAGCNNNNNNNN NAATGAANNNCAAAGTCTGNNNT GAGGATCCTCA-3' (Seq. I.D. No. 31) and 5'-CGGAATTCGACTCAGAA NNNNNNAACTTCAGANNNNNNATCNNNNNNNNN GTCTGAGGATCCTCA-3' (Seq. I.D. No. 32). Briefly, the two primers (each 200 pmol), purified by HPLC, were annealed at 70° C. for 5 minutes and cooled at 23° C. for 60 minutes. A Klenow fragment (5 U) was used for filling in with a dNTP mix (final concentration, 1 mM per each dNTP) at 23° C. for 60 minutes. The reaction was stopped with 1 μl of 0.5 M EDTA and the DNA was purified with ethanol precipitation. The resulting double-stranded DNA was digested with EcoRI and BamHI and re-purified by electrophoresis on non-denaturing polyacrylamide gels. The double-strand oligonucleotides were then ligated into the EcoRI-BamHI sites of the pBTM116 plasmid. The ligation mixtures were electroporated into the E. coli XL1-Blue MRF' (Stratagene) for the plasmid library. The large scale transformation was carried out as previously reported. The plasmid library was transformed into L40-strain cells (MATa, trp1, leu2, his3, ade2, LYS2: (lexAop)$^4$-HIS3, URA3: : (lexAop)$^8$-lacZ) carrying the plasmid pVP16-31 containing a FAP-1 cDNA (Sato, et al. 1995). Clones that formed on histidine-deficient medium (His$^+$) were transferred to plates containing 40 μg/ml X-gal to test for a blue reaction product (β-gal$^+$) in plate and filter assays. The clones selected by His$^+$ and β-gal$^+$ assay were tested for further analysis. The palindromic oligonucleotide, 5'-CGGAATTC-(NNN)$_{4-15}$-TGAGGATCCTCA-3' (Seq. I.D. No. 33), was used for the construction of the random peptide library.

2. Synthesis of Peptides

Peptides were automatically synthesized on an Advanced ChemTech ACT357 by analogy to published procedures (Schnorrenberg and Gerhardt, 1989). Wang resin (0.2–0.3 mmole scale) was used for each run and N$^\alpha$-Fmoc protection was employed for all amino acids. Deprotection was achieved by treatment with 20% piperidine/DMF and coupling was completed using DIC/HOBt and subsequent HBTU/DIEA. After the last amino acid was coupled, the growing peptide on the resin was acetylated with Ac$_2$O/DMF. The peptide was cleaved from the resin with concomitant removal of all protecting groups by treating with TFA. The acetylated peptide was purified by HPLC and characterized by FAB-MS and $^1$H-NMR.

3. Inhibition Asssay of Fas/FAP-1 Binding Using the C-terminal 15 Amino Acids of Fas.

HFAP-10 cDNA (Sato, et al. 1995) subcloned into the Bluescript vector pSK-II (Stratagene) was in vitro-translated from an internal methionine codon in the presence of $^{35}$S-L-methionine using a coupled in vitro transcription/translation system (Promega, TNT lysate) and T7 RNA polymerase. The resulting $^{35}$S-labeled protein was incubated with GST-Fas fusion proteins that had been immobilized on GST-Sepharose 4B affinity beads (Pharmacia) in a buffer containing 150 mM NaCl, 50 mM Tris [pH 8.0], 5 mM DTT, 2 mM EDTA, 0.1% NP-40, 1 mM PMSF, 50 μg/ml leupeptin, 1 mM Benzamidine, and 7 μg/ml pepstatin for 16 hours at 4° C. After washing vigorously 4 times in the same buffer, associated proteins were recovered with the glutathione-Sepharose beads by centrifugation, eluted into boiling Laemmli buffer, and analyzed by SDS-PAGE and fluorography.

4. Inhibition Assay of Terminal 15 Amino Acids of Fas and Inhibitory Effect of Fas/FAP-1 Binding Using Diverse Tripeptides.

In vitro-translated [$^{35}$S ]HFAP-1 was purified with a NAP-5 column (Pharmacia) and incubated with 3 μM of GST-fusion proteins for 16 hours at 4° C. After washing 4 times in the binding buffer, radioactivity incorporation was determined in a β counter. The percentage of binding inhibition was calculated as follows: percent inhibition= [radioactivity incorporation using GST-Fas (191–335) with peptides—radioactivity incorporation using GST-Fas (191–320) with peptides]/[radioactivity incorporation using GST-Fas (191–335) without peptides—radioactivity incorporation using GST-Fas (191–320) without peptides]. n=3.

5. Interaction of the C-terminal 3 Amino Acids of Fas with FAP-1 in Yeast and In Vitro.

The bait plasmids, pBTM116 (LexA)-SLV, -PLV, -SLY, and -SLA, were constructed and transformed into L40-strain with pVP16-FAP-1 or -ras. Six independent clones from each transformants were picked up for the analysis of growth on histidine-deficient medium. GST-Fas, -SLV, and PLV were purified with GST-Sepharose 4B affinity beads (Pharmacia). The methods for in vitro binding are described above.

6. Immuno-precipitation of Native Fas with GST-FAP-1 and Inhibition of Fas/FAP-1 Binding with Ac-SLV.

GST-fusion proteins with or without FAP-1 were incubated with cell extracts from Jurkat T-cells expressing Fas. The bound Fas was detected by Western analysis using anti-Fas monoclonal antibody (F22120, Transduction Laboratories) The tripeptides, Ac-SLV and Ac-SLY were used for the inhibition assay of Fas/FAP-1 binding.

7. Microinjection of Ac-SLV into the DLD-1 Cell Line.

DLD-1 human colon cancer cells were cultured in RPMI 1640 medium containing 10% FCS. For microinjection, cells were plated on CELLocate (Eppendorf) at 1×10$^5$ cells/2 ml in a 35 mm plastic culture dish and grown for 1 day. Just before microinjection, Fas monoclonal antibodies CH11 (MBL International) was added at the concentration of 500 ng/ml. All microinjection experiments were performed using an automatic microinjection system (Eppendorf transjector 5246, micro-manipulator 5171 and Femtotips) (Pantel, et al. 1995). Synthetic tripeptides were suspended in 0.1% (w/v) FITC-Dextran (Sigma)/K-PBS at the concentration of 100 mM. The samples were microinjected into the cytoplasmic region of DLD-1 cells. Sixteen to 20 hours postinjection, the cells were washed with PBS and stained with 10 μg/ml Hoechst 33342 in PBS. After incubation at 37° C. for 30 minutes, the cells were photographed and the cells showing condensed chromatin were counted as apoptotic.

8. Quantitation of Apoptosis in Microinjected DLD-1 Cells.

For each experiment, 25–100 cells were microinjected. Apoptosis of microinjected cells was determined by assessing morphological changes of chromatin using phase contrast and fluorescence microscopy (Wang, et al., 1995; McGahon, et al., 1995). The data are means +/– S.D. for two or three independent determinations.

Discussion

Figure 4A:
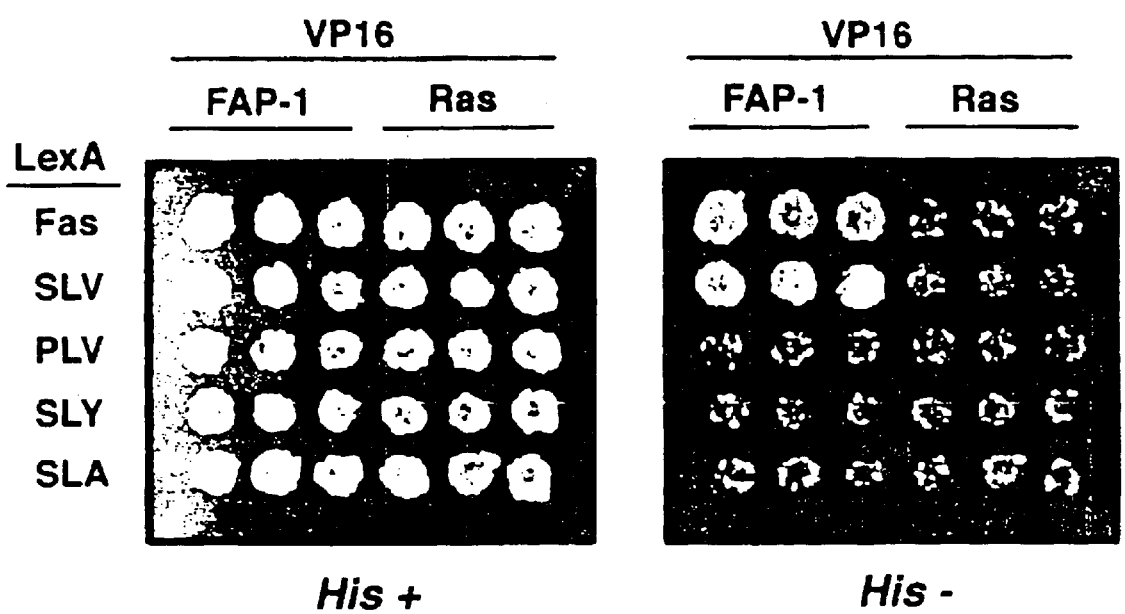
Figure 4B:

In order to identify the minimal peptide stretch in the C-terminal region of the Fas receptor necessary for FAP-1 binding, an in vitro inhibition assay of Fas/FAP-1 binding was used using a series of synthetic peptides as well as yeast two-hybrid system peptide libraries (FIG. 2A). First, semi-random libraries (based on the homology between human and rat Fas) (FIGS. 2B and 2C) of 15 amino acids fused to a LexA DNA binding domain were constructed and co-transformed into yeast strain L40 with pVP16-31 (Sato, et al. 1995) that was originally isolated as FAP-1. After the selection of 200 His$^+$ colonies from an initial screen of 5.0×10⁶ (Johnson, et al. 1986) transformants, 100 colonies that were β-galactosidase positive were picked for further analysis. Sequence analysis of the library plasmids encoding the C-terminal 15 amino acids revealed that all of the C-termini were either valine, leucine or isoleucine residues. Second, a random library of 4–15 amino acids fused to a LexA DNA binding domain was constructed and screened according to this strategy (FIG. 2D). Surprisingly, all of the third amino acid residues from the C-termini were serine, and the results of C-terminal amino acid analyses were identical to the screening of the semi-random cDNA libraries. No other significant amino acid sequences were found in these library screenings, suggesting that the motifs of the last three amino acids (tS—X—V/L/I) are very important for the association with the third PDZ domain of FAP-1 and play a crucial role in protein-protein interaction as well as for the regulation of Fas-induced apoptosis. To further confirm whether the last three amino acids are necessary and sufficient for Fas/FAP-1 binding, plasmids of the LexA-SLV, -PLV, -PLY, -SLY, and -SLA fusion proteins were constructed and co-transformed into yeast with pVP16-FAP-1. The results showed that only LexA-SLV associated with FAP-1, whereas LexA-PLV, -PLY, -SLY, and -SLA did not (FIG. 4A). In vitro binding studies using various GST-tripeptide fusions and in vitro-translated FAP-1 were consistent with these results (FIG. 4B).

In addition to yeast two-hybrid approaches, in vitro inhibition assay of Fas/FAP-1 binding was also used. First, a synthetic peptide of the C-terminal 15 amino acids was tested whether it could inhibit the binding of Fas and FAP-1 in vitro (FIG. 3A). The binding of in vitro-translated FAP-1 to GST-Fas was dramatically reduced and dependent on the concentration of the synthetic 15 amino acids of Fas. In contrast with these results, human PAMP peptide (Kitamura, et al. 1994) as a negative control had no effect on Fas/FAP-1 binding activity under the same biochemical conditions. Second, the effect of truncated C-terminal synthetic peptides of Fas on Fas/FAP-1 binding in vitro was examined. As shown in FIG. 3B, only the three C-terminal amino acids (Ac-SLV) were sufficient to obtain the same level of inhibitory effect on the binding of FAP-1 to Fas as achieved with the 4–15 synthetic peptides. Furthermore, Fas/FAP-1 binding was extensively investigated using the scanned tripeptides to determine the critical amino acids residues required for inhibition (FIG. 3C). The results revealed that the third amino acids residues from the C-terminus, and the C-terminal amino acids having the strongest inhibitory effect were either serine or threonine; and either valine, leucine, or isoleucine, respectively. However, there were no differences among the second amino acid residues from the C-terminus with respect to their inhibitory effect on Fas/FAP-1 binding. These results were consistent with those of the yeast two-hybrid system (FIGS. 2C and 2D). Therefore, it was concluded that the C-terminal three amino acids (SLV) are critical determinants of Fas binding to the third PDZ domain of FAP-1 protein.

To further substantiate that the PDZ domain interacts with tS/T—X—V/L/I under more native conditions, GST-fused FAP-1 proteins were tested for their ability to interact with Fas expressed in Jurkat T-cells. The results revealed that the tripeptide Ac-SLV, but not Ac-SLY, abolished in a dose-dependent manner the binding activity of FAP-1 to Fas proteins extracted from Jurkat T-cells (FIGS. 4C and 4D). This suggests that the C-terminal amino acids tSLV are the minimum binding site for FAP-1, and that the amino acids serine and valine are critical for this physical association.

To next examine the hypothesis that the physiological association between the C-terminal three amino acids of Fas and the third PDZ domain of FAP-1 is necessary for the in vivo function of FAP-1 as a negative regulator of Fas-mediated signal transduction, a microinjection experiment was employed with synthetic tripeptides in a colon cancer cell line, DLD-1, which expresses both Fas and FAP-1, and is resistant to Fas-induced apoptosis. The experiments involved the direct microinjection of the synthetic tripeptides into the cytoplasmic regions of single cells and the monitoring of the physiological response to Fas-induced apoptosis in vivo. The results showed that microinjection of Ac-SLV into DLD-1 cells dramatically induced apoptosis in the presence of Fas-monoclonal antibodies (CH11, 500 ng/ml) (FIGS. 5A, 5E and FIG. 6), but that microinjection of Ac-SLY and PBS/K did not (FIGS. 5B, 5F and FIG. 6). These results strongly support the hypothesis that the physical association of FAP-1 with the C-terminus of Fas is essential for protecting cells from Fas-induced apoptosis.

In summary, it was found that the C-terminal SLV of Fas is alone necessary and sufficient for binding to the third PDZ domain of FAP-1. Secondly, it is proposed that the new consensus motif of tS/T—X—V/L/I for such binding to the PDZ domain, instead of tS/T—X—V. It is therefore possible that FAP-1 plays important roles for the modulation of signal transduction pathways in addition to its physical interaction with Fas. Thirdly, it is demonstrated that the targeted induction of Fas-mediated apoptosis in colon cancer cells by direct microinjection of the tripeptide Ac-SLV. Further investigations including the identification of a substrate(s) of FAP-1 and structure-function analysis will provide insight to the potential therapeutic applications of Fas/FAP-1 interaction in cancer as well as provide a better understanding of the inhibitory effect of FAP-1 on Fas-mediated signal transduction.

Second Series of Experiments

FAP-1 was originally identified as a membrane-associated protein tyrosine phosphatase which binds to the C-terminus of Fas, and possesses six PDZ domains (also known as DHR domain or GLGF repeat). PDZ domain has recently been shown as a novel module for specific protein-protein interaction, and it appears to be important in the assembly of membrane proteins and also in linking signaling molecules in a multiprotein complex. In recent comprehensive studies, it was found that the third PDZ domain of FAP-1 specifically recognized the sequence motif t(S/T)—X—V and interacts with the C-terminal three amino acids SLV of Fas (FIG. 9). In order to investigate the possibility that FAP-1 also interacts with the C-terminal region of p75NGFR (FIG. 8), an in vitro binding assay, was performed as well as, a yeast two-hybrid analysis by using a series of deletion mutants of p75NGFR. The results revealed that the C-terminal cytoplasmic region of p75NGFR, which is highly conserved among all species, interacts with FAP-1 (FIG. 10). Furthermore, the C-terminal three amino acids SPV of p75NGFR were necessary and sufficient for the interaction with the third PDZ domain of FAP-1 (FIGS. 11A and 11B) Since FAP-1 expression was found highest in fetal brain, these findings imply that interaction of FAP-1 with p75NGFR plays an important role for signal transduction pathway via p75NGFR in neuronal cells as well as in the formation of the initial signal-transducing complex for p75NGFR.

References

1. Arenkov, P., et al. *Biotechniques* 27(4): 123–31 (2000).
2. Banville, D., et al. *J. Biol. Chem.* 269: 22320–22327 (1994).
3. Boldin, M. P., et al. *J. Biol. Chem.* 270: 7795–7798 (1995).

4. Camerini, D., et al. *J. Immunol.* 147: 3165–3169 (1991).
5. Chao, M. V. and B. L. Hempstead *TINS* 18: 321–326 (1995).
6. Chinnaiyan, A. M., et al. *Cell* 81: 505–512 (1995).
7. Cho, K. O., et al. *Neuron* 9: 929–942 (1992).
8. Conboy, J. G., et al. *J. Biol. Chem.* 266: 8273–8280 (1991).
9. Doyle, D. A., et al. *Cell* 85: 1067–1076 (1996).
10. Funayama, N., et al. *J. Cell Biol.* 115: 1039-1048 (1991).
11. Gould, K. L., et al. *EMBO J.* 8: 4133–4142 (1989).
12. Gu, M. X., et al. *Proc. Natl. Acad. Sci. U.S.A.* 88: 5867–5871 (1991).
13. Hill, D. E., et al. *Meth. Enzymol.* 155, 558–568 (1987).
14. Ito, N., and Nagata, S. *J. Biol. Chem.* 268: 10932–10937 (1993).
15. Itoh, N., et al. *Cell* 66: 233–243 (1991).
16. Johnson, D., et al. *Cell* 47: 545–554 (1986).
17. Kim, E., et al. *Nature* 378: 85–88 (1995).
18. Kischkel, F. C., et al. *EMBO J.* 14: 5579–5588 (1995).
19. Kitamura, K., et al. *FEBS Lett.* 351: 35–37 (1994).
20. Kornau, H. C., et al. *Science* 269:1737–1740 (1995).
21. Lankes, W. T., and Furthmayr, H. *Proc. Natl. Acad. Sci. U.S.A.* 88: 8297–8301 (1991).
22. Maekawa, K., et al. *FEBS Letters* 337: 200–206 (1994).
23. Mallett, S., et al. *EMBO J.* 9: 1063–1068 (1990).
24. Matsumine, A., et al. *Science* 272: 1020–1023 (1996).
25. McGahon, A. J., et al. *Meth. Cell Biol.* 46: 153–185 (1995).
26. Mendoza, L. G., et al. *Biotechniques* 27(4): 778–88 (1999).
27. Pantel, K., et al. *J. Natl. Cancer Inst.* 87: 1162–1168 (1995).
28. Rouleau, G., et al. *Nature* 363: 515–521 (1993).
29. Rowe, C. A., et al. *Anal Chem.* 71(2): 433–39 (1999).
30. Sambrook, J., et al. *Molecular Cloning; a laboratory manual, Second Edition.* Cold Spring Harbor Laboratory Press (1989).
31. Saras, J., et al. *J. Biol. Chem.* 269, 24082–24089 (1994).
32. Sato, T., et al. *Science* 268: 411–415 (1995).
33. Schnorrenberg, G. and Gerhardt H. *Tetrahedron* 45: 7759–7764 (1989).
34. Silzel, J. W., et al. *Clin. Chem.* 44(9): 2036–43 (1998).
35. Smith, C. A., et al. *Cell* 73: 1349–1360 (1993).
36. Stamenkovic, I., et al. *EMBO J.* 8: 1403–1410 (1989).
37. Stanger, B. Z., et al. *Cell* 81: 513–523 (1995).
38. Takahashi, T., et al. *Cell* 76: 969–976 (1994).
39. Vogel, W., et al. *Science* 259: 1611–1614 (1993).
40. Watanabe-Fukunaga, R., et al. *Nature* 356: 314–317 (1992).
41. Wang, X. W., et al. *Cancer Res.* 55: 6012–6016 (1995).
42. Westendorp, M. O., et al. *Nature* 375: 497–500 (1995).
43. Woods, D. F. and Bryant, P. J. *Cell* 66: 451–464 (1991).
44. Yang, Q., and Tonks, N. K. *Proc. Natl. Acad. Sci. U.S.A.* 88: 5949–5953 (1991).

What is claimed is:

1. A method of preparing a protein array, comprising the steps of;
   (a) depositing on a substrate an array of first proteins, each first protein comprising a PDZ domain; and
   (b) applying a second protein, which comprises an amino acid sequence (S/T)—X—(V/I/L)—COOH, to the array of first proteins, the amino acid sequence (S/T)—X—(V/I/L)—COOH of the second protein, for each of the first proteins, binding to the PDZ domain of the first protein,
   wherein each hyphen represents a peptide bond, each parenthesis encloses amino acids which are alternatives to one other, each slash within such parentheses separates the alternative amino acids, and the X represent any amino acid which is selected from the group consisting of alanine, cysteine, aspartic acid, glutamic acid, phenylalanine, glycine, histidine, isoleucine, lysine, leucine, methionine, asparagine, proline, glutamine, arginine, serine, threonine, valine, tryptophan and tyrosine.

2. The method of claim 1, wherein the amino acid sequence (S/T)—X—(V/I/L) is fused to the C-terminal of the second protein.

3. The method of claim 1, wherein at least one of the first proteins deposited in step (a) is in a soluble buffer.

4. The method of claim 1, wherein at least one of the first proteins deposited in step (a) is immobilized in a gel.

5. The method of claim 1, wherein the substrate includes a plurality of microwells contained therein, and the first proteins are deposited in step (a) into the microwells.

6. The method of claim 1, wherein the substrate includes a glass plate, and the first proteins are printed onto the glass plate in step (a).

7. The method of claim 1, wherein the substrate includes a glass plate and a plurality of gel pads on the glass plate, and the first proteins are deposited in step (a) onto the gal pads.

8. The method of claim 1, wherein the first proteins are deposited on the substrate by a robot.

9. A method of preparing a protein array, comprising the steps of:
   (a) depositing on a substrate an array of a first protein, the first protein comprising a PDZ domain; and
   (b) applying a plurality of second proteins, each of which comprises an amino acid sequence (S/T)—X—(V/I/L)—COOH, to the elements of the first protein array, for each of the second proteins, the amino acid sequence (S/T)—X—(V/I/L)—COOH of the second protein binding to the PDZ domain of the first protein in the array element,
   wherein each hyphen represents a peptide bond, each parenthesis encloses amino acids which are alternatives to one other, each slash within such parentheses separates the alternative amino acids, and the X represents any amino acid which is selected from the group consisting of alanine, cysteine, aspartic acid, glutamic acid, phenylalanine, glycine, histidine, isoleucine, lysine, leucine, methionine, asparagine, proline, glutamine, arginine, serine, threonine, valine, tryptophan and tyrosine.

10. The method of claim 9, wherein the amino acid sequence (S/T)—X—(V/I/L) is fused to the C-terminal of the second protein.

11. The method of claim 9, wherein the first protein deposited in step (a) is in a soluble buffer.

12. The method of claim 9, wherein the first protein deposited in step (a) is immobilized in a gel.

13. The method of claim 9, wherein the substrate includes a plurality of microwells contained therein, and the first protein is deposited in step (a) into the microwells.

14. The method of claim 9, wherein the substrate includes a glass plate, and the first protein array is printed onto the glass plate in step (a).

15. The method of claim 9, wherein the substrate includes a glass plate and a plurality of gel pads on the glass plate, and the first protein is deposited in step (a) onto the gel pads.

16. The method of claim 9, wherein the first protein is deposited on the substrate by a robot.

* * * * *